US011768200B2

(12) United States Patent
Porreca et al.

(10) Patent No.: US 11,768,200 B2
(45) Date of Patent: *Sep. 26, 2023

(54) METHODS FOR MAINTAINING THE INTEGRITY AND IDENTIFICATION OF A NUCLEIC ACID TEMPLATE IN A MULTIPLEX SEQUENCING REACTION

(71) Applicant: Molecular Loop Biosciences, Inc., Cambridge, MA (US)

(72) Inventors: Gregory Porreca, Cambridge, MA (US); Mark Umbarger, Brookline, MA (US); George Church, Brookline, MA (US)

(73) Assignee: Molecular Loop Biosciences, Inc., Cambridge, MA (US)

( * ) Notice: Subject to any disclaimer, the term of this patent is extended or adjusted under 35 U.S.C. 154(b) by 244 days.

This patent is subject to a terminal disclaimer.

(21) Appl. No.: 17/339,527

(22) Filed: Jun. 4, 2021

(65) Prior Publication Data
US 2021/0293796 A1   Sep. 23, 2021

Related U.S. Application Data

(60) Continuation of application No. 17/149,504, filed on Jan. 14, 2021, now Pat. No. 11,041,852, which is a continuation of application No. 14/854,629, filed on Sep. 15, 2015, now Pat. No. 11,041,851, which is a division of application No. 13/081,660, filed on Apr. 7, 2011, now Pat. No. 9,163,281.

(60) Provisional application No. 61/426,817, filed on Dec. 23, 2010.

(51) Int. Cl.
*C12Q 1/6869* (2018.01)
*G01N 33/543* (2006.01)

(52) U.S. Cl.
CPC ......... *G01N 33/543* (2013.01); *C12Q 1/6869* (2013.01); *C12Q 2525/155* (2013.01); *C12Q 2525/179* (2013.01); *C12Q 2525/191* (2013.01); *G01N 2458/10* (2013.01)

(58) Field of Classification Search
CPC ...................... C12Q 1/6869; C12Q 2525/179
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,988,617 A | 1/1991 | Landegren et al. |
| 5,060,980 A | 10/1991 | Johnson et al. |
| 5,210,015 A | 5/1993 | Gelfand et al. |
| 5,234,809 A | 8/1993 | Boom et al. |
| 5,242,794 A | 9/1993 | Whiteley et al. |
| 5,348,853 A | 9/1994 | Wang et al. |
| 5,434,049 A | 7/1995 | Okano et al. |
| 5,459,307 A | 10/1995 | Klotz, Jr. |
| 5,486,686 A | 1/1996 | Zdybel, Jr. et al. |
| 5,491,224 A | 2/1996 | Bittner et al. |
| 5,494,810 A | 2/1996 | Barany et al. |
| 5,567,583 A | 10/1996 | Wang et al. |
| 5,583,024 A | 12/1996 | McElroy et al. |
| 5,604,097 A | 2/1997 | Brenner |
| 5,636,400 A | 6/1997 | Young |
| 5,674,713 A | 10/1997 | McElroy et al. |
| 5,695,934 A | 12/1997 | Brenner |
| 5,700,673 A | 12/1997 | McElroy et al. |
| 5,701,256 A | 12/1997 | Marr et al. |
| 5,830,064 A | 11/1998 | Bradish et al. |
| 5,846,719 A | 12/1998 | Brenner et al. |
| 5,863,722 A | 1/1999 | Brenner |
| 5,866,337 A | 2/1999 | Schon |
| 5,869,252 A | 2/1999 | Bouma et al. |
| 5,869,717 A | 2/1999 | Frame et al. |
| 5,871,921 A | 2/1999 | Landegren et al. |
| 5,888,788 A | 3/1999 | De Miniac |
| 5,942,391 A | 8/1999 | Zhang et al. |
| 5,971,921 A | 10/1999 | Timbel |
| 5,993,611 A | 11/1999 | Moroney, III et al. |
| 5,994,056 A | 11/1999 | Higuchi |
| 6,020,127 A | 2/2000 | Mackenzie et al. |
| 6,033,854 A | 3/2000 | Kurnit et al. |
| 6,033,872 A | 3/2000 | Bergsma et al. |
| 6,100,099 A | 8/2000 | Gordon et al. |
| 6,138,077 A | 10/2000 | Brenner |
| 6,150,516 A | 11/2000 | Brenner et al. |
| 6,171,785 B1 | 1/2001 | Higuchi |
| 6,172,214 B1 | 1/2001 | Brenner |
| 6,172,218 B1 | 1/2001 | Brenner |

(Continued)

FOREIGN PATENT DOCUMENTS

| | | |
|---|---|---|
| EP | 1 321 477 A1 | 6/2003 |
| EP | 1 564 306 A2 | 8/2005 |

(Continued)

OTHER PUBLICATIONS

Zhao, 2009, PGA4genomics for comparative genome assembly based on genetic algorithm optimization, Genomics 94 (4):284-6.
Zheng, 2011, iAssembler: a package for de novo assembly of Roche-454/Sanger transcriptome sequences, BMC Bioinformatics 12:453.
Zhou, 2014, Bias from removing read duplication in ultra-deep sequencing experiments, Bioinformatics 30(8):1073-1080.
Zhulidov, 2004, Simple cDNA normalization using kamchatka crab duplex-specific nuclease, Nucl Acids Res 32(3): e37, 8 pages.
Zimmerman, 2010, A novel custom resequencing array for dilated cardiomyopathy, Gen Med 12(5):268-78.

(Continued)

*Primary Examiner* — Teresa E Strzelecka
(74) *Attorney, Agent, or Firm* — COOLEY LLP; Ivor R. Elrifi; Edith Hang Yu Cheng

(57) ABSTRACT

The invention generally relates to methods for maintaining the integrity and identification of a nucleic acid template in a multiplex sequencing reaction. In certain embodiments, methods of the invention involve obtaining a template nucleic acid, incorporating a pair of sequence identifiers into the template, and sequencing the template.

6 Claims, 3 Drawing Sheets

(56) References Cited

U.S. PATENT DOCUMENTS

| | | |
|---|---|---|
| 6,197,508 B1 | 3/2001 | Stanley |
| 6,197,574 B1 | 3/2001 | Miyamoto et al. |
| 6,210,891 B1 | 4/2001 | Nyren et al. |
| 6,223,128 B1 | 4/2001 | Allex et al. |
| 6,235,472 B1 | 5/2001 | Landegren et al. |
| 6,235,475 B1 | 5/2001 | Brenner et al. |
| 6,235,501 B1 | 5/2001 | Gautsch et al. |
| 6,235,502 B1 | 5/2001 | Weissman et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,360,235 B1 | 3/2002 | Tilt et al. |
| 6,361,940 B1 | 3/2002 | Van Ness et al. |
| 6,403,320 B1 | 6/2002 | Read et al. |
| 6,462,254 B1 | 10/2002 | Vernachio et al. |
| 6,489,105 B1 | 12/2002 | Matlashewski et al. |
| 6,558,928 B1 | 5/2003 | Landegren |
| 6,569,920 B1 | 5/2003 | Wen et al. |
| 6,582,938 B1 | 6/2003 | Su et al. |
| 6,585,938 B1 | 7/2003 | Machida et al. |
| 6,613,516 B1 | 9/2003 | Christians et al. |
| 6,714,874 B1 | 3/2004 | Myers et al. |
| 6,716,580 B2 | 4/2004 | Gold et al. |
| 6,719,449 B1 | 4/2004 | Laugharn, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,858,412 B2 | 2/2005 | Willis et al. |
| 6,911,345 B2 | 6/2005 | Quake et al. |
| 6,913,879 B1 | 7/2005 | Schena |
| 6,927,024 B2 | 8/2005 | Dodge et al. |
| 6,941,317 B1 | 9/2005 | Chamberlin et al. |
| 6,948,843 B2 | 9/2005 | Laugharn, Jr. et al. |
| 7,034,143 B1 | 4/2006 | Preparata et al. |
| 7,041,481 B2 | 5/2006 | Anderson et al. |
| 7,049,077 B2 | 5/2006 | Yang |
| 7,057,026 B2 | 6/2006 | Barnes et al. |
| 7,071,324 B2 | 7/2006 | Preparata et al. |
| 7,074,564 B2 | 7/2006 | Landegren |
| 7,074,586 B1 | 7/2006 | Cheronis et al. |
| 7,115,400 B1 | 10/2006 | Adessi et al. |
| 7,169,560 B2 | 1/2007 | Lapidus et al. |
| 7,211,390 B2 | 5/2007 | Rothberg et al. |
| 7,232,656 B2 | 6/2007 | Balasubramanian et al. |
| 7,244,559 B2 | 7/2007 | Rothberg et al. |
| RE39,793 E | 8/2007 | Brenner |
| 7,264,929 B2 | 9/2007 | Rothberg et al. |
| 7,282,337 B1 | 10/2007 | Harris |
| 7,297,518 B2 | 11/2007 | Quake et al. |
| 7,320,860 B2 | 1/2008 | Landegren et al. |
| 7,323,305 B2 | 1/2008 | Leamon et al. |
| 7,335,762 B2 | 2/2008 | Rothberg et al. |
| 7,351,528 B2 | 4/2008 | Landegren |
| 7,393,665 B2 | 7/2008 | Brenner |
| 7,510,829 B2 | 3/2009 | Faham et al. |
| 7,523,117 B2 | 4/2009 | Zhang et al. |
| 7,537,889 B2 | 5/2009 | Sinha et al. |
| 7,537,897 B2 | 5/2009 | Brenner et al. |
| 7,544,473 B2 | 6/2009 | Brenner |
| 7,582,431 B2 | 9/2009 | Drmanac et al. |
| 7,598,035 B2 | 10/2009 | Macevicz |
| 7,629,151 B2 | 12/2009 | Gold et al. |
| 7,642,056 B2 | 1/2010 | Ahn et al. |
| 7,666,593 B2 | 2/2010 | Lapidus |
| 7,700,323 B2 | 4/2010 | Willis et al. |
| 7,774,962 B1 | 8/2010 | Ladd |
| 7,776,616 B2 | 8/2010 | Heath et al. |
| RE41,780 E | 9/2010 | Anderson et al. |
| 7,790,388 B2 | 9/2010 | Landegren et al. |
| 7,809,509 B2 | 10/2010 | Milosavljevic |
| 7,835,871 B2 | 11/2010 | Kain et al. |
| 7,862,999 B2 | 1/2011 | Zheng et al. |
| 7,865,534 B2 | 1/2011 | Genstruct |
| 7,883,849 B1 | 2/2011 | Dahl |
| 7,957,913 B2 | 6/2011 | Chinitz et al. |
| 7,960,120 B2 | 6/2011 | Rigatti et al. |
| 7,985,716 B2 | 7/2011 | Yershov et al. |
| 7,993,880 B2 | 8/2011 | Willis et al. |
| 8,024,128 B2 | 9/2011 | Rabinowitz et al. |
| 8,114,027 B2 | 2/2012 | Triva |
| 8,165,821 B2 | 4/2012 | Zhang |
| 8,209,130 B1 | 6/2012 | Kennedy et al. |
| 8,283,116 B1 | 10/2012 | Bhattacharyya et al. |
| 8,462,161 B1 | 6/2013 | Barber |
| 8,463,895 B2 | 6/2013 | Arora et al. |
| 8,474,228 B2 | 7/2013 | Adair et al. |
| 8,496,166 B2 | 7/2013 | Burns et al. |
| 8,529,744 B2 | 9/2013 | Marziali et al. |
| 8,738,300 B2 | 5/2014 | Porreca et al. |
| 8,778,609 B1 | 7/2014 | Umbarger |
| 8,812,422 B2 | 8/2014 | Nizzari et al. |
| 8,847,799 B1 | 9/2014 | Kennedy et al. |
| 8,976,049 B2 | 3/2015 | Kennedy et al. |
| 9,074,244 B2 | 7/2015 | Sparks et al. |
| 9,115,387 B2 | 8/2015 | Umbarger |
| 9,163,281 B2 | 10/2015 | Porreca et al. |
| 9,228,233 B2 | 1/2016 | Kennedy et al. |
| 9,292,527 B2 | 3/2016 | Kennedy et al. |
| 9,535,920 B2 | 1/2017 | Kennedy et al. |
| 9,567,639 B2 | 2/2017 | Oliphant et al. |
| 9,677,124 B2 | 6/2017 | Umbarger |
| 10,066,259 B2 | 9/2018 | Gore et al. |
| 10,202,637 B2 | 2/2019 | Umbarger |
| 10,227,635 B2 | 3/2019 | Umbarger et al. |
| 10,604,799 B2 | 3/2020 | Porreca et al. |
| 10,683,533 B2 | 6/2020 | Umbarger et al. |
| 11,041,851 B2 | 6/2021 | Porreca et al. |
| 11,041,852 B2 | 6/2021 | Porreca et al. |
| 2001/0007742 A1 | 7/2001 | Landergren |
| 2001/0046673 A1 | 11/2001 | French et al. |
| 2002/0001800 A1 | 1/2002 | Lapidus |
| 2002/0040216 A1 | 4/2002 | Dumont et al. |
| 2002/0042052 A1 | 4/2002 | Nilsen et al. |
| 2002/0091666 A1 | 7/2002 | Rice et al. |
| 2002/0164629 A1 | 11/2002 | Quake et al. |
| 2002/0172954 A1 | 11/2002 | Mao et al. |
| 2002/0182609 A1 | 12/2002 | Arcot |
| 2002/0187496 A1 | 12/2002 | Andersson et al. |
| 2002/0190663 A1 | 12/2002 | Rasmussen |
| 2003/0166057 A1 | 9/2003 | Hildebrand et al. |
| 2003/0175709 A1 | 9/2003 | Murphy et al. |
| 2003/0177105 A1 | 9/2003 | Xiao et al. |
| 2003/0203370 A1 | 10/2003 | Yakhini et al. |
| 2003/0208454 A1 | 11/2003 | Rienhoff et al. |
| 2003/0224384 A1 | 12/2003 | Sayood et al. |
| 2004/0029264 A1 | 2/2004 | Robbins |
| 2004/0053275 A1 | 3/2004 | Shafer |
| 2004/0106112 A1 | 6/2004 | Nilsson et al. |
| 2004/0121373 A1 | 6/2004 | Friedlander et al. |
| 2004/0142325 A1 | 7/2004 | Mintz et al. |
| 2004/0152108 A1 | 8/2004 | Keith et al. |
| 2004/0161773 A1 | 8/2004 | Rogan et al. |
| 2004/0170965 A1 | 9/2004 | Scholl et al. |
| 2004/0171051 A1 | 9/2004 | Holloway |
| 2004/0175719 A1 | 9/2004 | Christians |
| 2004/0197813 A1 | 10/2004 | Hoffman et al. |
| 2004/0209299 A1 | 10/2004 | Pinter et al. |
| 2005/0003369 A1 | 1/2005 | Christians et al. |
| 2005/0026204 A1 | 2/2005 | Landegren |
| 2005/0032095 A1 | 2/2005 | Wigler et al. |
| 2005/0048505 A1 | 3/2005 | Fredrick et al. |
| 2005/0059048 A1 | 3/2005 | Gunderson et al. |
| 2005/0100900 A1 | 5/2005 | Kawashima et al. |
| 2005/0112590 A1 | 5/2005 | Boom et al. |
| 2005/0186589 A1 | 8/2005 | Kowalik et al. |
| 2005/0214811 A1 | 9/2005 | Margulies et al. |
| 2005/0244879 A1 | 11/2005 | Schumm et al. |
| 2005/0250147 A1 | 11/2005 | Macevicz |
| 2005/0272065 A1 | 12/2005 | Lakey et al. |
| 2006/0008824 A1 | 1/2006 | Ronaghi et al. |
| 2006/0019304 A1 | 1/2006 | Hardenbol et al. |
| 2006/0024681 A1 | 2/2006 | Smith et al. |
| 2006/0030536 A1 | 2/2006 | Yu et al. |

(56) References Cited

U.S. PATENT DOCUMENTS

| | | |
|---|---|---|
| 2006/0078894 A1 | 4/2006 | Winkler et al. |
| 2006/0149047 A1 | 7/2006 | Nanduri et al. |
| 2006/0177837 A1 | 8/2006 | Borozan et al. |
| 2006/0183132 A1 | 8/2006 | Fu et al. |
| 2006/0192047 A1 | 8/2006 | Goossen |
| 2006/0195269 A1 | 8/2006 | Yeatman et al. |
| 2006/0246500 A1 | 11/2006 | Browne |
| 2006/0263789 A1 | 11/2006 | Kincaid |
| 2006/0281098 A1 | 12/2006 | Miao et al. |
| 2006/0286577 A1 | 12/2006 | Jia |
| 2006/0292585 A1 | 12/2006 | Nautiyal et al. |
| 2006/0292611 A1 | 12/2006 | Berka et al. |
| 2007/0009925 A1 | 1/2007 | Fang et al. |
| 2007/0020640 A1 | 1/2007 | McCloskey et al. |
| 2007/0042369 A1 | 2/2007 | Reese et al. |
| 2007/0092883 A1 | 4/2007 | Schouten et al. |
| 2007/0114362 A1 | 5/2007 | Feng et al. |
| 2007/0128624 A1 | 6/2007 | Gormley et al. |
| 2007/0161013 A1 | 7/2007 | Hantash |
| 2007/0162983 A1 | 7/2007 | Hesterkamp et al. |
| 2007/0166705 A1 | 7/2007 | Milton et al. |
| 2007/0212704 A1 | 9/2007 | Dong et al. |
| 2007/0225487 A1 | 9/2007 | Nilsson et al. |
| 2007/0238122 A1 | 10/2007 | Allbritton et al. |
| 2007/0244675 A1 | 10/2007 | Shai et al. |
| 2007/0264653 A1 | 11/2007 | Berlin et al. |
| 2008/0003142 A1 | 1/2008 | Link et al. |
| 2008/0014589 A1 | 1/2008 | Link et al. |
| 2008/0076118 A1 | 3/2008 | Tooke et al. |
| 2008/0081330 A1 | 4/2008 | Kahvejian |
| 2008/0085836 A1 | 4/2008 | Kearns et al. |
| 2008/0090239 A1 | 4/2008 | Shoemaker et al. |
| 2008/0125324 A1 | 5/2008 | Petersdorf et al. |
| 2008/0176209 A1 | 7/2008 | Muller et al. |
| 2008/0269068 A1 | 10/2008 | Church et al. |
| 2008/0280955 A1 | 11/2008 | McCamish |
| 2008/0293589 A1 | 11/2008 | Shapero |
| 2009/0009904 A1 | 1/2009 | Yasuna et al. |
| 2009/0019156 A1 | 1/2009 | Mo et al. |
| 2009/0026082 A1 | 1/2009 | Rothberg et al. |
| 2009/0029385 A1 | 1/2009 | Christians et al. |
| 2009/0035777 A1 | 2/2009 | Kokoris et al. |
| 2009/0042206 A1 | 2/2009 | Schneider et al. |
| 2009/0098551 A1 | 4/2009 | Landers et al. |
| 2009/0099041 A1 | 4/2009 | Church et al. |
| 2009/0105081 A1 | 4/2009 | Rodesch et al. |
| 2009/0119313 A1 | 5/2009 | Pearce |
| 2009/0127589 A1 | 5/2009 | Rothberg et al. |
| 2009/0129647 A1 | 5/2009 | Dimitrova et al. |
| 2009/0156412 A1 | 6/2009 | Boyce, IV et al. |
| 2009/0163366 A1 | 6/2009 | Nickerson et al. |
| 2009/0181389 A1 | 7/2009 | Li et al. |
| 2009/0191565 A1 | 7/2009 | Lapidus et al. |
| 2009/0192047 A1 | 7/2009 | Parr et al. |
| 2009/0202984 A1 | 8/2009 | Cantor |
| 2009/0203014 A1 | 8/2009 | Wu et al. |
| 2009/0220955 A1 | 9/2009 | Verrant |
| 2009/0226975 A1 | 9/2009 | Sabot et al. |
| 2009/0233814 A1 | 9/2009 | Bashkirov et al. |
| 2009/0298064 A1 | 12/2009 | Batzoglou et al. |
| 2009/0301382 A1 | 12/2009 | Patel |
| 2009/0318310 A1 | 12/2009 | Liu et al. |
| 2010/0035243 A1 | 2/2010 | Muller et al. |
| 2010/0035252 A1 | 2/2010 | Rothberg et al. |
| 2010/0063742 A1 | 3/2010 | Hart et al. |
| 2010/0069263 A1 | 3/2010 | Shendure et al. |
| 2010/0076185 A1 | 3/2010 | Adey et al. |
| 2010/0086914 A1 | 4/2010 | Bentley et al. |
| 2010/0086926 A1 | 4/2010 | Craig et al. |
| 2010/0105107 A1 | 4/2010 | Hildebrand et al. |
| 2010/0137143 A1 | 6/2010 | Rothberg et al. |
| 2010/0137163 A1 | 6/2010 | Link et al. |
| 2010/0143908 A1 | 6/2010 | Gillevet |
| 2010/0159440 A1 | 6/2010 | Messier et al. |
| 2010/0188073 A1 | 7/2010 | Rothberg et al. |
| 2010/0196911 A1 | 8/2010 | Hoffman et al. |
| 2010/0197507 A1 | 8/2010 | Rothberg et al. |
| 2010/0216151 A1 | 8/2010 | Lapidus et al. |
| 2010/0216153 A1 | 8/2010 | Lapidus et al. |
| 2010/0227329 A1 | 9/2010 | Cuppens |
| 2010/0248984 A1 | 9/2010 | Shaffer et al. |
| 2010/0282617 A1 | 11/2010 | Rothberg et al. |
| 2010/0285578 A1 | 11/2010 | Selden et al. |
| 2010/0297626 A1 | 11/2010 | Mckernan et al. |
| 2010/0300559 A1 | 12/2010 | Schultz et al. |
| 2010/0300895 A1 | 12/2010 | Nobile et al. |
| 2010/0301042 A1 | 12/2010 | Kahlert |
| 2010/0301398 A1 | 12/2010 | Rothberg et al. |
| 2010/0304982 A1 | 12/2010 | Hinz et al. |
| 2010/0311061 A1 | 12/2010 | Korlach et al. |
| 2010/0330619 A1 | 12/2010 | Willis et al. |
| 2011/0004413 A1 | 1/2011 | Carnevali et al. |
| 2011/0009278 A1 | 1/2011 | Kain et al. |
| 2011/0015863 A1 | 1/2011 | Pevzner et al. |
| 2011/0021366 A1 | 1/2011 | Chinitz et al. |
| 2011/0034342 A1 | 2/2011 | Fox |
| 2011/0092375 A1 | 4/2011 | Zamore et al. |
| 2011/0098193 A1 | 4/2011 | Kingsmore et al. |
| 2011/0117544 A1 | 5/2011 | Lexow |
| 2011/0159499 A1 | 6/2011 | Hindson et al. |
| 2011/0166029 A1 | 7/2011 | Margulies et al. |
| 2011/0224105 A1 | 9/2011 | Kurn et al. |
| 2011/0230365 A1 | 9/2011 | Rohlfs et al. |
| 2011/0257889 A1 | 10/2011 | Klammer et al. |
| 2011/0288780 A1 | 11/2011 | Rabinowitz et al. |
| 2011/0301042 A1 | 12/2011 | Steinmann et al. |
| 2012/0015050 A1 | 1/2012 | Abkevich et al. |
| 2012/0021930 A1 | 1/2012 | Schoen et al. |
| 2012/0046877 A1 | 2/2012 | Hyland et al. |
| 2012/0059594 A1 | 3/2012 | Hatchwell et al. |
| 2012/0074925 A1 | 3/2012 | Oliver |
| 2012/0079980 A1 | 4/2012 | Taylor et al. |
| 2012/0115736 A1 | 5/2012 | Bjornson et al. |
| 2012/0164630 A1 | 6/2012 | Porreca et al. |
| 2012/0165202 A1 | 6/2012 | Porreca et al. |
| 2012/0179384 A1 | 7/2012 | Kuramitsu et al. |
| 2012/0214678 A1 | 8/2012 | Rava et al. |
| 2012/0216151 A1 | 8/2012 | Sarkar et al. |
| 2012/0236861 A1 | 9/2012 | Ganeshalingam et al. |
| 2012/0245041 A1 | 9/2012 | Brenner et al. |
| 2012/0252020 A1 | 10/2012 | Shuber |
| 2012/0252684 A1 | 10/2012 | Selifonov et al. |
| 2012/0258461 A1 | 10/2012 | Weisbart |
| 2012/0270212 A1 | 10/2012 | Rabinowitz et al. |
| 2012/0270739 A1 | 10/2012 | Rava et al. |
| 2013/0129755 A1 | 5/2013 | Song |
| 2013/0130921 A1 | 5/2013 | Gao et al. |
| 2013/0178378 A1 | 7/2013 | Hatch et al. |
| 2013/0183672 A1 | 7/2013 | De Laat et al. |
| 2013/0222388 A1 | 8/2013 | McDonald |
| 2013/0268206 A1 | 10/2013 | Porreca et al. |
| 2013/0268474 A1 | 10/2013 | Nizzari et al. |
| 2013/0274146 A1 | 10/2013 | Umbarger et al. |
| 2013/0275103 A1 | 10/2013 | Struble et al. |
| 2013/0288242 A1 | 10/2013 | Stoughton et al. |
| 2013/0323730 A1 | 12/2013 | Curry et al. |
| 2013/0332081 A1 | 12/2013 | Reese et al. |
| 2013/0337447 A1 | 12/2013 | Porreca et al. |
| 2013/0344096 A1 | 12/2013 | Chiang et al. |
| 2014/0129201 A1 | 5/2014 | Kennedy et al. |
| 2014/0136120 A1 | 5/2014 | Colwell et al. |
| 2014/0206552 A1 | 7/2014 | Rabinowitz et al. |
| 2014/0222349 A1 | 8/2014 | Higgins et al. |
| 2014/0228226 A1 | 8/2014 | Yin et al. |
| 2014/0255931 A1 | 9/2014 | Porreca et al. |
| 2014/0274741 A1 | 9/2014 | Hunter et al. |
| 2014/0308667 A1 | 10/2014 | Umbarger |
| 2014/0318274 A1 | 10/2014 | Zimmerman et al. |
| 2014/0342354 A1 | 11/2014 | Evans et al. |
| 2014/0361022 A1 | 12/2014 | Finneran |
| 2015/0051085 A1 | 2/2015 | Vogelstein et al. |
| 2015/0056613 A1 | 2/2015 | Kural |
| 2015/0111208 A1 | 4/2015 | Umbarger et al. |
| 2015/0178445 A1 | 6/2015 | Cibulskis et al. |

(56) References Cited

U.S. PATENT DOCUMENTS

| | | |
|---|---|---|
| 2015/0258170 A1 | 9/2015 | McCabe et al. |
| 2015/0299767 A1 | 10/2015 | Armour et al. |
| 2015/0310163 A1 | 10/2015 | Kingsmore et al. |
| 2015/0354003 A1 | 12/2015 | Umbarger |
| 2016/0003812 A1 | 1/2016 | Porreca et al. |
| 2016/0034638 A1 | 2/2016 | Spence et al. |
| 2016/0068889 A1 | 3/2016 | Gole et al. |
| 2016/0188793 A1 | 6/2016 | Muzzey et al. |
| 2016/0210486 A1 | 7/2016 | Porreca et al. |
| 2016/0251719 A1 | 9/2016 | Umbarger |
| 2017/0044610 A1 | 2/2017 | Johnson |
| 2017/0129964 A1 | 5/2017 | Cheung |
| 2017/0183731 A1 | 6/2017 | Mann et al. |
| 2017/0275676 A1 | 9/2017 | Umbarger |
| 2018/0371533 A1 | 12/2018 | Gore et al. |
| 2019/0233881 A1 | 8/2019 | Umbarger et al. |
| 2020/0181696 A1 | 6/2020 | Porreca et al. |

FOREIGN PATENT DOCUMENTS

| | | | |
|---|---|---|---|
| EP | 2425240 | A2 | 3/2012 |
| EP | 2 437 191 | A2 | 4/2012 |
| EP | 2716766 | A1 | 4/2014 |
| JP | H11318478 | A | 11/1999 |
| JP | 2008528040 | A | 7/2008 |
| WO | 95/011995 | A1 | 5/1995 |
| WO | 1996/019586 | A1 | 6/1996 |
| WO | 98/014275 | A1 | 4/1998 |
| WO | 98/044151 | A1 | 10/1998 |
| WO | 00/018957 | A1 | 4/2000 |
| WO | 02/093453 | A2 | 11/2002 |
| WO | 2004/018497 | A2 | 3/2004 |
| WO | 2004/083819 | A2 | 9/2004 |
| WO | 2005/003304 | A2 | 1/2005 |
| WO | 2006/084132 | A2 | 8/2006 |
| WO | 2007/010251 | A2 | 1/2007 |
| WO | 2007/061284 | A1 | 5/2007 |
| WO | 2007/107717 | A1 | 9/2007 |
| WO | 2007/123744 | A2 | 11/2007 |
| WO | 2007/135368 | A2 | 11/2007 |
| WO | 2008067551 | A2 | 6/2008 |
| WO | 2009/036525 | A2 | 3/2009 |
| WO | 2009/076238 | A2 | 6/2009 |
| WO | 2010/024894 | A1 | 3/2010 |
| WO | 2010/115154 | A1 | 10/2010 |
| WO | 2010/126614 | A2 | 11/2010 |
| WO | 2011/006020 | A1 | 1/2011 |
| WO | 2011066476 | A1 | 6/2011 |
| WO | 2011067378 | A1 | 6/2011 |
| WO | 2011/102998 | A2 | 8/2011 |
| WO | 2011/155833 | A2 | 12/2011 |
| WO | 2012/006291 | A2 | 1/2012 |
| WO | 2012/040387 | A1 | 3/2012 |
| WO | 2012/051208 | A2 | 4/2012 |
| WO | 2012/087736 | A1 | 6/2012 |
| WO | 2012/109500 | A2 | 8/2012 |
| WO | 2012/134884 | A1 | 10/2012 |
| WO | 2012/149171 | A1 | 11/2012 |
| WO | 2012/170725 | A2 | 12/2012 |
| WO | 2013/058907 | A1 | 4/2013 |
| WO | 2013/148496 | A1 | 10/2013 |
| WO | 2013/177086 | A1 | 11/2013 |
| WO | 2013/191775 | A2 | 12/2013 |
| WO | 2014/052909 | A2 | 4/2014 |
| WO | 2014/074246 | A1 | 5/2014 |
| WO | 2015/119941 | A2 | 8/2015 |

OTHER PUBLICATIONS

Zimran, 1990, A glucocerebrosidase fusion gene in Gaucher disease, J Clin Invest 85:219-222.
Zuckerman, 1987, Efficient methods for attachment of thiol specific probes to the 3'-ends of synthetic oligodeoxyribonucleotides, Nucl Acid Res 15(13):5305-5321.
Sonnhammer, 2002, Orthology, paralogy and proposed classification for paralog subtypes, Trends in Genetics, 18 (12):619-620.
Spanu, 2010, Genome expansion and gene loss in powdery mildew fungi reveal tradeoffs in extreme parasitism, Science 330(6010):1543-46.
Sproat, 1987, The synthesis of protected 5'-mercapto-2',5'-dideoxyribonucleoside-3'-O-phosphoramidites; uses of 5'-mercapto-oligodeoxynucleotides, Nucl Acid Res 15:4837-4848.
Streit, 2003, CFTR gene: molecular analysis in patients from South Brazil, Molecular Genetics and Metabolism 78:259-264.
Strom, 2005, Mutation detection, interpretation, and applications in the clinical laboratory setting, Mutat Res 573:160-67.
Summerer, 2009, Enabling technologies of genomic-scale sequence enrichment for targeted high-throughput sequencing, Genomics 94(6):363-8.
Summerer, 2010, Targeted High Throughput Sequencing of a Cancer-Related Exome Subset by Specific Sequence Capture With a Fully Automated Microarray Platform, Genomics 95(4):241-246.
Sunnucks, 1996, Microsatellite and chromosome evolution of parthenogenetic sitobion aphids in Australia, Genetics 144:747-756.
Tan, 2014, Clinical outcome of preimplantation genetic diagnosis and screening using next generation sequencing, GigaScience 3(30):1-9.
Tarhini, 2018, Predictive and on-treatment monitoring biomarkers in advanced melanoma: Moving toward personalized medicine, Cancer Treatment Reviews, 71:8-18.
Thauvin-Robinet, 2009, The very low penetrance of cystic fibrosis for the R117H mutation: a reappraisal for genetic counseling and newborn screening, J Med Genet 46:752-758.
Thiyagarajan, 2006, PathogenMIPer: a tool for the design of molecular inversion probes to detect multiple pathogens, BMC Bioinformatics 7:500, 10 pages.
Thompson, 1994, Clustal W: improving the sensitivity of progressive mulitple sequence alignment through sequence weighting, position-specific gap penalties and weight matrix choice, Nuc Acids Res 22:4673-80.
Thompson, 2011, The properties and applications of single-molecule DNA sequencing, Genome Biol 12(2):217, 10 pages.
Thorstenson, 1998, An Automated Hydrodynamic Process for Controlled, Unbiased DNA Shearing, Genome Res 8(8):848-855.
Thorvaldsdottir, 2012, Integrative Genomics Viewer (IGV): high-performance genomics data visualization and exploration, Brief Bioinform 24(2):178-92.
Tkachuk, 1990, Detection of bcr-abl Fusion in Chronic Myelogeneous Leukemia by in Situ Hybridization, Science 250:559-562.
Tobler, 2005, The SNPlex Genotyping System: A Flexible and Scalable Platform for SNP Genotyping, J Biomol Tech 16(4):398-406.
Tokino, 1996, Characterization of the human p57 KIP2 gene: alternative splicing, insertion/deletion polymorphisms in VNTR sequences in the coding region, and mutational analysis, Human Genetics 96:625-31.
Treangen, 2011, Repetitive DNA and next-generation sequencing: computational challenges and solutions, Nat Rev Gen 13(1):36-46.
Turner, 2009, Massively parallel exon capture and library-free resequencing across 16 genomes, Nat Meth 6:315-316.
Turner, 2009, Methods for genomic partitioning, Ann Rev Hum Gen 10:263-284.
Umbarger, 2013, Detecting contamination in Next Generation DNA sequencing libraries, American Society of Human Genetics 63rd Annual Meeting, Abstract, Oct. 22, 2013, 2 pages.
Umbarger, 2014, Next-generation carrier screening, Gen Med 16(2):132-140.
Veeneman, 2012, Oculus: faster sequence alignment by streaming read compression, BMC Bioinformatics 13:297, 8 pages.
Wahl, 1979, Efficient transfer of large DNA fragments from agarose gels to diazobenzyloxymethyl-paper and rapid hybridization by using dextran sulfate, PNAS 76:3683-3687.
Wallace, 1979, Hybridization of synthetic oligodeoxyribonucteotides to dp x 174DNA:the effect of single base pair mismatch, Nucl Acids Res 6:3543-3557.
Wallace, 1987, Oligonucleotide probes for the screening of recombinant DNA libraries, Meth Enz 152:432-442.

(56) References Cited

OTHER PUBLICATIONS

Wang, 2005, Allele quantification using molecular inversion probes (MIP), Nucleic Acids Res 33(21):e183, 14 pages.
Wang, 2007, Analysis of molecular inversion probe performance for allele copy number determination, Genome Biology, 8(11):R246.1-R246.14.
Warner, 1996, A general method for the detection of large CAG repeat expansions by fluorescent PCR, J Med Genet 33(12):1022-6.
Warren, 2007, Assembling millions of short DNA sequences using SSAKE, Bioinformatics, 23:500-501.
Waszak, 2010, Systematic inference of copy-number genotypes from personal genome sequencing data reveals extensive olfactory gene content diversity, PLoS Comp Biol 6(11):e1000988, 20 pages.
Watson, 2004, Cystic fibrosis population carrier screening: 2004 revision of American College of Medical Genetics mutation panel, Genetics in Medicine 6(5):387-391.
Williams, 2003, Restriction endonucleases classification, properties, and applications, Mol Biotechnol 23(3):225-43.
Wirth, 1999, Quantitative analysis of survival motor neuron copies, Am J Hum Genet 64:1340-1356.
Wittung, 1997, Extended DNA-Recognition Repertoire of Peptide Nucleic Acid (PNA): PNA-dsDNA Triplex Formed with Cytosine-Rich Homopyrimidine PNA, Biochemistry 36:7973-7979.
Wu, 1998, Sequencing regular and labeled oligonucleotides using enzymatic digestion and ionspray mass spectrometry, Anal Biochem 263:129-138.
Wu, 2001, Improved oligonucleotide sequencing by alkaline phosphatase and exonuclease digestions with mass spectrometry, Anal Biochem 290:347-352.
Xu, 2012, FastUniq: A fast de novo duplicates removal tool for paired short reads, PLoS One 7(12):e52249, 6 pages.
Yau, 1996, Accurate diagnosis of carriers of deletions and duplications in Duchenne/Becker muscular dystrophy by fluorescent dosage analysis, J Med Gen 33(7):550-8.
Ye, 2009, Pindel: a pattern growth approach to detect break points of large deletions and medium size insertions from paired-end short reads, Bioinformatics 25(21):2865-2871.
Yershov, 1996, DNA analysis and diagnostics on oligonucleotide microchips, PNAS 93:4913-4918.
Yoo, 2009, Applications of DNA microarray in disease diagnostics, J Microbiol Biotech19(7):635-46.
Yoon, 2014, MicroDuMIP: target-enrichment technique for microarray-based duplex molecular inversion probes, Nucl Ac Res 43(5):e28, 9 pages.
Yoshida, 2004, Role of BRCA1 and BRCA2 as regulators of DNA repair, transcription, and cell cycle in response to DNA damage, Cancer Science 95(11)866-71.
Yu, 2007, A novel set of DNA methylation markers in urine sediments for sensitive/specific detection of bladder cancer, Clin Cancer Res 13(24):7296-7304.
Yuan, 1981, Structure and mechanism of multifunctional restriction endonucleases, Ann Rev Biochem 50:285-319.
Zerbino, 2008, Velvet: Algorithms for de novo short read assembly using de Bruijn graphs, Genome Research 18(5):821-829.
Zhang, 2011, Is Mitochondrial tRNAphe Variant m.593T.Ca Synergistically Pathogenic Mutation in Chinese LHON Families with m.11778G.A? PLoS One 6(10):e26511, 8 pages.
Lipman, 1985, Rapid and sensitive protein similarity searches, Science 227(4693):1435-41.
Liu, 2012, Comparison of next-generation sequencing systems, J Biomed Biotech 2012:251364, 12 pages.
Llopis, 1998, Measurement of cytosolic, mitochondrial, and Golgi pH in single living cells with green fluorescent proteins, PNAS 95(12):6803-08.
Ma, 2006, Application of real-time polymerase chain reaction (RT-PCR), J Am Soc 1-15.
MacArthur, 2014, Guidelines for investigating causality of sequence variants in human disease, Nature 508:469-76.
Maddalena, 2005, Technical standards and guidelines: molecular genetic testing for ultra-rare disorders, Genet Med 7:571-83.

Malewicz, 2010, Pregel: a system for large-scale graph processing, Proc. ACM SIGMOD Int Conf Mgmt Data 135-46.
Mamanova, 2010, Target-enrichment strategies for next-generation sequencing, Nat Meth 7(2):111-118.
Margulies, 2005, Genome sequencing in micro-fabricated high-density picotiter reactors, Nature, 437:376-380.
Marras, 1999, Multiplex detection of single-nucleotide variations using molecular beacons, Genetic Analysis: Biomolecular Engineering 14:151, 6 pages.
Maxam, 1977, A new method for sequencing DNA, PNAS, 74:560-564.
May 1988, How Many Species Are There on Earth?, Science 241(4872):1441-9.
McDonnell, 2007, Antisepsis, disinfection, and sterilization: types, action, and resistance, p. 239.
McKenna, 2010, The Genome Analysis Toolkit: A MapReduce framework for analyzing next-generation DNA sequencing data, Genome Research 20:1297-1303.
Messiaen, 1999, Exon 10b of the NF1 gene represents a mutational hotspot and harbors a recurrent missense mutation Y489C associated with aberrant splicing, Genetics in Medicine, 1(6):248-253.
Meyer, 2007, Targeted high-throughput sequencing of tagged nucleic acid samples, Nucleic Acids Research 35(15):e97, 5 pages.
Meyer, 2008, Parallel tagged sequencing on the 454 platform, Nat Protocol 3(2):267-278.
Meyer, 2008, Parallel tagged sequencing on the 454 platform, Nature Protocols, 3(2):267-278.
Miesenbock, 1998, Visualizing secretion and synaptic transmission with pH-sensitive green fluorescent proteins, Nature 394(6689):192-95.
Miller, 2010, Assembly algorithms for next-generation sequencing data, Genomics 95:315-327.
Mills, 2010, Mapping copy number variation by population-scale genome sequencing, Nature 470(7332):59-65.
Miner, 2004, Molecular barcodes detect redundancy and contamination in hairpin-bisulfite PCR, Nucl Acids Res 32 (17):e135, 4 pages.
Minton, 2011, Mutation Surveyor: software for DNA sequence analysis, Meth Mol Biol 688:143-53.
Miyake, 2009, PIK3CA gene mutations and umplification in uterine cancers, Canc Lett 261:120-126.
Miyazaki, 2009, Characterization of deletion breakpoints in patients with dystrophinopathy carrying a deletion of exons 45-55 of the Duchenne muscular dystrophy (DMD) gene, J Hum Gen 54:127-30.
Mockler, 2005, Applications of DNA tiling arrays for whole-genome analysis, Genomics 85(1):1-15.
Mohammed, 2012, DELIMINATE—a fast and efficient methods for loss-less compression of genomice sequences, Bioinformatics 28(19):2527-2529.
Moudrianakis, 1965, Base Sequence Determination in Nucleic Acids with the Electron Microscope, III. Chemistry and Microscopy of Guanine-Labeled DNA, PNAS, 53:564-71.
Mullan, 2002, Multiple sequence alignment-the gateway to further analysis, Brief Bioinform 3(3):303-5.
Munne, 2012, Preimplantation genetic diagnosis for aneuploidy and translocations using array comparative genomic hybridization, Curr Genomics 13(6):463-470.
Nan, 2006, A novel CFTR mutation found in a Chinese patient with cystic fibrosis, Chinese Med J 119(2):103-9.
Narang, 1979, Improved phosphotriester method for the synthesis of gene fragments, Meth Enz 68:90-98.
Nelson, 1989, Bifunctional oligonucleotide probes synthesized using a novel CPG support are able to detect single base pair mutations, Nucl Acids Res 17(18):7187-7194.
Ng, 2009, Targeted capture and massively parallel sequencing of 12 human exomes, Nature 461(7261):272-6.
Nicholas, 2002, Strategies for multiple sequence alignment, Biotechniques 32:572-91.
Nickerson, 1990, Automated DNA diagnostics using an ELISA-based oligonucleotide ligation assay, PNAS 87:8923-7.
Nielsen, 1999, Peptide Nucleic Acids, Protocols and Applications (Norfolk: Horizon Scientific Press, 1-19).

(56) References Cited

OTHER PUBLICATIONS

Nilsson, 2006, Analyzing genes using closing and replicating circles, Trends in Biotechnology 24:83-8.
Ning, 2001, SSAHA: a fast search method for large DNA databases, Genome Res 11(10):1725-9.
Nordhoff, 1993, Ion stability of nucleic acids in infrared matrix-assisted laser desorption/ ionization mass spectrometry, Nucl Acid Res 21(15):3347-57.
Nuttle, 2013, Rapid and accurate large-scale genotyping of duplicated genes and discovery of interlocus gene conversions, Nat Meth 10(9):903-909.
Nuttle, 2014, Resolving genomic disorder-associated breakpoints within segmental DNA duplications using massively parallel sequencing, Nat Prot 9(6):1496-1513.
O'Roak, 2012, Multiplex targeted sequencing identifies recurrently mutated genes in autism spectrum disorders, Science 338(6114):1619-1622.
Oefner, 1996, Efficient random sub-cloning of DNA sheared in a recirculating point-sink flow system, Nucleic Acids Res 24(20):3879-3886.
Oka, 2006, Detection of loss of heterozygosity in the p53 gene in renal cell carcinoma and bladder cancer using the polymerase chain reaction, Mol Carcinogenesis 4(1):10-13.
Okoniewski, 2013, Precise breakpoint localization of large genomic deletions using PacBio and Illumina next-generation sequencers, Biotechniques 54(2):98-100.
Okou, 2007, Microarray-based genomic selection for high-throughput reseuqencing, Nat Meth 4(11):907-909.
Oliphant, 2002, BeadArray technology: enabling an accurate, cost-effective approach to high-throughput genotyping, Biotechniques Suppl:56-8, 60-1.
Ordahl, 1976, Sheared DNA fragment sizing: comparison of techniques, Nucleic Acids Res 3:2985-2999.
Ostrer, 2001, A genetic profile of contemporary Jewish populations, Nat Rev Genet 2(11):891-8.
Harris, 2008, Single-molecule DNA sequencing of a viral genome, Science 320(5872):106-9.
Heger, 2006, Protonation of Cresol Red in Acidic Aqueous Solutions Caused by Freezing, J Phys Chem B 110(3):1277-1287.
Heid, 1996, Real time quantitative PCR, Genome Res 6:986-994.
Hiatt, 2013, Single molecule molecular inversion probes for targeted, high-accuracy detection of low-frequency variation, Genome Res 23:843-54.
Hodges, 2007, Genome-wide in situ exon capture for selective resequencing, Nat Genet 39(12):1522-7.
Holland, 2008, BioJava: an open-source framework for bioinformatics, Bioinformatics 24(18):2096-2097.
Homer, 2008, Resolving Individuals Contributing Trace Amounts of DNA to Highly Complex Mixtures Using High-Density SNP Genotyping Microarrays. PLoS One 4(8):e1000167, 9 pages.
Homer, 2009, BFAST: An alignment tool for large scale genome resequencing, PLoS One 4(11):e7767, 12 pages.
Housley, 2009, SNP discovery and haplotype analysis in the segmentally duplicated DRD5 coding region, Ann Hum Genet 73(3):274-282.
Huang, 2008, Comparative analysis of common CFTR polymorphisms poly-T, TGrepeats and M470V in a healthy Chinese population, World J Gastroenterol 14(12):1925-30.
Husemann, 2009, Phylogenetic Comparative Assembly, Algorithms in Bioinformatics: 9th International Workshop, Salzberg & Warnow, Eds. Springer-Verlag, Berlin, Heidelberg, pp. 145-156,.
Ilumina, 2010, De Novo assembly using Illumina reads, Technical Note, 8 pages.
International Human Genome Sequencing Consortium, 2004, Finishing the euchromatic sequence of the human genome, Nature 431:931-945.
Iqbal, 2012, De novo assembly and genotyping of variants using colored de Bruijn graphs, Nature Genetics 44:226-232.
Isosomppi, 2009, Disease-causing mutations in the CLRN1 gene alter normal CLRN1 protien trafficking to the plasma membrane, Mol Vis 15:1806-1818.
Jaijo, 2010, Microarray-based mutation analysis of 183 Spanish families with Usher syndrome, Invest Ophthalmol Vis Sci 51(3):1311-7.
Jensen, 2001, Orthologs and paralogs—we need to get it right, Genome Biol 2(8):1002-1002.3.
Jones, 2008, Core signaling pathways in human pancreatic cancers revealed by global genomic analyses, Science 321(5897):1801-1806.
Kambara, 1988, Optimization of Parameters in a DNA Sequenator Using Fluorescence Detection, Nature Biotechnology 6:816-821.
Kennedy, 2013, Accessing more human genetic variation with short sequencing reads, American Society of Human Genetics 63rd Annual Meeting, Abstract, Oct. 22, 2013, 2 pages.
Kent, 2002, BLAT—The BLAST-like alignment tool, Genome Res 12(4): 656-664.
Kerem, 1989, Identification of the cystic fibrosis gene: genetic analysis, Science 245:1073-1080.
Kinde, 2012, FAST-SeqS: a simple an effective method for detection of aneuploidy by massively parallel sequencing, PLoS One 7(7):e41162, 8 pages.
Kircher, 2010, High-througput DNA sequencing—concepts and limitations, Bioassays 32:524-36.
Kirpekar, 1994, Matrix assisted laser desorption/ionization mass spectrometry of enzymatically synthesized RNA up to 150 kDa, Nucl Acids Res 22:3866-3870.
Klein, 2011, LOCAS—A low coverage sequence assembly tool for re-sequencing projects, PLOoS One 6(8):e23455, 10 pages.
Kneen, 1998, Green fluorescent protein as a noninvasive intracellular pH indicator, Biophys J 74(3):1591-99.
Koboldt, 2009, VarScan: variant detection in massively parallel sequencing of individual and pooled samples, Bioinformatics 25:2283-85.
Krawitz, 2010, Microindel detection in short-read sequence data, Bioinformatics 26(6):722-729.
Kreindler, 2010, Cystic fibrosis: exploiting its genetic basis in the hunt for new therapies, Pharmacol Ther 125(2):219-229.
Krishnakumar, 2008, A comprehensive assay for targeted multiplex amplification of human DNA sequences, PNAS 105:9296-301.
Kumar, 2010, Comparing de novo assemblers for 454 transcriptome data, Genomics 11:571 (12 pages).
Kurtz, 2004, Versatile and open software for comparing large genomes, Genome Biol 5:R12, 9 pages.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25, 10 pages.
Larkin, 2007, Clustal W and Clustal X version 2.0, Bioinformatics, 23(21):2947-2948.
Lecompte, 2001, Multiple alignment of complete sequences (MACS) in the post-genomic era, Gene 270(1-2):17-30.
Li, 2003, DNA binding and cleavage by the periplasmic nuclease Vvn: a novel structure with a known active site, EMBO J 22(15):4014-4025.
Li, 2008, SOAP: short oligonucleotide alignment program, Bioinformatics 24(5):713-14.
Li, 2009, Fast and accurate short read alignment with Burrows-Wheeler transform, Bioinformatics, 25 (14):1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, Fast and accurate long-read alignment with Burrows-Wheeler transform, Bioinformatics 26(5):589-95.
Li, 2011, Improving SNP discovery by base alignment quality, Bioinformatics 27:1157, 2 pages.
Li, 2011, Single nucleotide polymorphism genotyping and point mutation detection by ligation on microarrays, J Nanosci Nanotechnol 11(2):994-1003.

(56) References Cited

OTHER PUBLICATIONS

Li, 2012, A new approach to detecting low-level mutations in next-generation sequence data, Genome Biol 13:1-15.
Li, 2014, HUGO: Hierarchical mUlti-reference Genome cOmpression for aligned reads, JAMIA 21:363-373.
Lin, 2008, ZOOM! Zillions Of Oligos Mapped, Bioinformatics 24:2431-2437.
Lin, 2010, A molecular inversion prove assay for detecting alternative splicing, BMC Genomics 11(712):1-14.
Lin, 2012, Development and evaluation of a reverse dot blot assay for the simultaneous detection of common alpha and beta thalassemia in Chinese, Blood Cells Molecules, and Diseases 48(2):86-90.
Abravaya, 1995, Detection of point mutations with a modified ligase chain reaction (Gap-LCR), Nucleic Acids Research, 23(4):675-682.
Adey, 2010, Rapid, low-input, low-bias construction of shotgun fragment libraries by high-density in vitro transposition, Genome Biol 11:R119, 17 pages.
Ageno, 1969, The alkaline denaturation of DNA, Biophys J 9(11):1281-1311.
Agrawal, 1990, Site-specific functionalization of oligodeoxynucleotides for non-radioactive labelling, Tetrahedron Let 31:1543-1546.
Akhras, 2007, Connector inversion probe technology: A powerful one-primer multiplex DNA amplification system for numerous scientific applications, PLoSOne 2(9):e915.
Akhras, 2007, PathogenMip Assay: a multiplex pathogen detection assay, PLoS One 2:e2230.
Alazard, 2002, Sequencing of production-scale synthetic oligonucleotides by enriching for coupling failures using matrix-assisted laser desorption/ ionization time of-flight mass spectrometry, Anal Biochem 301:57-64.
Alazard, 2006, Sequencing oligonucleotides by enrichment of coupling failures using matrix-assisted laser desorption/ionization time of-flight mass spectrometry, Curr Protoc Nucleic Acid Chem, Chapter 10, Unit 10:1-7.
Albert, 2007, Direct selection of human genomic loci by microarray hybridization, Nature Methods 4(11):903-5.
Aljanabi, 1997, Universal and rapid salt-extraction of high quality genomic DNA for PCR-based techniques, Nucl. Acids Res 25:4692-4693.
Antonarakis and the Nomenclature Working Group, 1998, Recommendations for a nomenclature system for human gene mutations, Human Mutation 11:1-3.
Archer, 2014, Selective and flexible depletion of problematic sequences from RNA-seq libraries at the cDNA stage, BMC Genomics 15(1):401, 9 pages.
Ball, 2009, Targeted and genome-scale strategies reveal gene-body methylation signatures in human cells, Nat Biotech 27:361-8.
Balzer, 2013, Filtering duplicate reads from 454 pyrosequencing data, Bioinformatics 29(7):830-836.
Barany, 1991, Genetic disease detection and DNA amplification using cloned thermostable ligase, PNAS 88:189-193.
Barany, 1991, The Ligase Chain Reaction in a PCR World, Genome Research 1:5-16.
Bau, 2008, Targeted next-generation sequencing by specific capture of multiple genomic loci using low-volume microfluidic DNA arrays, Analytical and Bioanal Chem 393(1):171-5.
Beer, 1962, Determination of base sequence in nucleic acids with the electron microscope: visibility of a marker, PNAS 48(3):409-416.
Bell, 2011, Carrier testing for severe childhood recessive diseases by next-generation sequencing, Sci Trans Med 3 (65ra4), 15 pages.
Benner, 2001, Evolution, language and analogy in functional genomics, Trends Genet 17:414-8.
Bentzley, 1996, Oligonucleotide sequence and composition determined by matrix-assisted laser desorption/ionization, Anal Chem 68:2141-2146.
Bentzley, 1998, Base specificity of oligonucleotide digestion by calf spleen phosphodiesterase with matrix-assisted laser desorption ionization analysis, Anal Biochem 258:31-37.
Bhangale, 2006, Automating resequencing-based detection of insertion-deletion polymorphisms, Nature Genetics 38:1457-1462.
Bickle, 1993, Biology of DNA Restriction, Microbiol Rev 57(2):434-50.
Blasczyk, 1996, Sequence analysis of the 2nd intron revealed common sequence motifs providing the means for a unique sequencing based typing protocol of the HLA-A locus, Tissue Antigens, 47:102-110.
Bonfield, 2013, Compression of FASTQ and SAM format sequencing data, PLoS One 8(3):e59190, 10 pages.
Bose, 2012, BIND—An algorithm for loss-less compression of nucleotide sequence data, J Biosci 37(4):785-789.
Boyden, 2013, High-throughput screening for SMN1 copy number loss by next-generation sequencing, American Society of Human Genetics 63rd Annual Meeting, Abstract, Oct. 22, 2013, 2 pages.
Boyer, 1971, DNA restriction and modification mechanisms in bacteria, Ann Rev Microbiol 25:153-76.
Braasch, 2001, Locked nucleic acid (LNA): fine-tuning the recognition of DNA and RNA, Chemistry & Biology 8(1):1-7.
Braslavsky, 2003, Sequence information can be obtained from single DNA molecules, PNAS 100:3960-4.
Brinkman, 2004, Splice Variants as Cancer Biomarkers, Clin Biochem 37:584-594.
Brison, 1982, General method for cloning amplified DNA by differential screening, Mol Cell Biol 2(5):578-587.
Brown, 1979, Chemical synthesis and cloning of a tyrosine tRNA gene, Methods Enzymol, 68:109-51.
Browne, 2002, Metal ion-catalyzed nucleic Acid alkylation and fragmentation, J Am Chem Soc 124(27):7950-7962.
Brownstein, 2014, An international effort towards developing standards for best practices in analysis, interpretation and reporting of clinical genome sequencing results in the CLARITY Challenge, Genome Biol 15:R53, 8 pages.
Bunyan, 2004, Dosage analysis of cancer predisposition genes by multiplex ligation-dependent probe amplification, British Journal of Cancer, 91(6):1155-59.
Burrow, 1994, A block-sorting lossless data compression algorithm, Technical Report 124, Digital Equipment Corporation, CA., 24 pages.
Carpenter, 2013, Pulling out the 1%: whole-genome capture for the targeted enrichment of ancient DNA sequencing libraries, Am J Hum Genet 93(5):852-864.
Caruthers, 1985, Gene synthesis machines: DNA chemistry and its uses, Science 230:281-285.
Castellani, 2008, Consenses on the use of and interpretation of cystic fibrosis mutation analysis in clinical practice, J Cyst Fib 7:179-196.
Challis, 2012, An integrative variant analysis suite for whole exome next-generation sequencing data, BMC Informatics 13(8):1-12.
Chan, 2011, Natural and engineered nicking endonucleases-from cleavage mechanism to engineering of strand-specificity, Nucl Acids Res 39(1):1-18.
Chen, 2010, Identification of racehorse and sample contamination by novel 24-plex STR system, Forensic Sci Int: Genetics 4:158-167.
Chennagiri, 2013, A generalized scalable database model for storing and exploring genetic variations detected using sequencing data, American Society of Human Genetics 63rd Annual Meeting, Abstract, Oct. 22, 2013, 2 pages.
Chevreux, 1999, Genome sequence assembly using trace signals and additional sequence information, Proc GCB 99:45-56.
Chirgwin, 1979, Isolation of biologically active ribonucleic acid from sources enriched in ribonuclease, Biochemistry, 18:5294-99.
Choe, 2010, Novel CFTR Mutations in a Korean Infant with Cystic Fibrosis and Pancreatic Insufficiency, J Korean Med Sci 25:163-5.
Chou, 2010, DNA Sequence Capture and Enrichment by Microarray Followed by Next-Generation Sequencing for Targeted Resequencing: Neurofibromatosis Type 1 Gene as a Model, Clinical Chemistry, 56(1):62-72.
Ciotti, 2004, Triplet repeat prmied PCR (TP PCR) in molecular diagnostic testing for Friedrich ataxia, J Mol Diag 6(4):285-9.

(56) References Cited

OTHER PUBLICATIONS

Cock, 2010, The Sanger FASTQ file format for sequences with quality scores, and the Solexa/Illumina FASTQ variants, Nucleic Acids Res 38(6):1767-1771.
Collins, 2004, Finishing the euchromatic sequence of the human genome, Nature 431(7011):931-45.
Craig, 1997, Removal of repetitive sequences from FISH probes, Hum Genet 100:472.
Cremers, 1998, Autosomal Recessive Retinitis Pigmentosa and Cone-Rod Dystrophy Caused by Splice Site Mutations in the Stargardt's Disease Gene ABCR, Hum Mol Gen 7(3):355-362.
Cronin, 1996, Cystic Fibrosis Mutation Detection by Hybridization to Light-Generated DNA Probe Arrays Human Mutation 7:244-255.
Dahl, 2005, Multiplex amplification enabled by selective circularization of large sets of genomic DNA fragments, Nucleic Acids Res 33(8):e71, 7 pages.
Daly, 2007, Multiplex Assay for Comprehensive Genotyping of Genes Involved in Drug Metabolism, Excretion, and Transport, Clinical Chemistry, 53:7:1222-1230.
Danecek, 2011, The variant call format and VCFtools, Bioinformatics 27(15):2156-2158.
De la Bastide, 2007, Assembling genome DNA sequences with PHRAP, Current Protocols in Bioinformatics 17:11.4.1-11.4.15, 15 pages.
Delcher, 1999, Alignment of whole genomes, Nuc Acids Res 27(11):2369-2376.
Den Dunnen, 2003, Mutation Nomenclature, Curr Prot Hum Genet 7.13.1-7.13.8, 8 pages.
Deng, 2009, targeted bisulfite sequencing reveals changes in DNA methylation, Nat Biotech 27(4):353-360.
Deng, 2012, Supplementary Material, Nature Biotechnology, S1-1-S1-1 1, Retrieved from the Internet on Oct. 24, 2012, 12 pages.
Deorowicz, 2013, Data compression for sequencing data, Alg for Mole Bio 8:25, 13 pages.
Diep, 2012, Library-free methylation sequencing with bisulfite padlock probes, Nature Methods 9:270-272 (and supplemental information).
DiGuistini, 2009, De novo sequence assembly of a filamentous fungus using Sanger, 454 and Illumina sequence data, Genome Biology, 10:R94, 12 pages.
Dolinsek, 2013, Depletion of unwanted nucleic acid templates by selection cleavage: LNAzymes, catalytically active oligonucleotides containing locked nucleic acids, open a new window for detecting rare microbial community members, App Env Microbiol 79(5):1534-1544.
Dong, 2011, Mutation surveyor: An in silico tool for sequencing analysis, Methods Mol Biol 760:223-37.
Dou, 2012, Reference-free SNP calling: improved accuracy by preventing incorrect calls from repetitive genomic regions, Biology Direct 7:17.
Drmanac, 1992, Sequencing by hybridization: towards an automated sequencing of one million M13 clones arrayed on membranes, Elctrophoresis 13:566-573.
Dudley, 2009, A quick guide for developing effective bioinformatics programming skills, PLoS Comp Biol 5(12):e1000589, 7 pages.
Ericsson, 2008, A dual-tag microarray platform for high-performance nucleic acid and protein analyses, Nucl Acids Res 36:e45, 9 pages.
Fares, 2008, Carrier frequency of autosomal-recessive disorders in the Ashkenazi Jewish population: should the rationale for mutation choice for screening be reevaluated?, Prenatal Diagnosis 28:236-41.
Faulstich, 1997, A sequencing method for RNA oligonucleotides based on mass spectrometry, Anal Chem 69:4349-4353.
Faust, 2014, SAMBLASTER: fast duplicate marking and structural variant read extraction, Bioinformatics published online May 7, 2014, 2 pages.
Fitch, 1970, Distinguishing homologs from analogous proteins, Syst Biol 19(2):99-113.

Flaschker, 2007, Description of the mutations in 15 subjects with variant forms of maple syrup urine disease, J Inherit Metab Dis 30:903-909.
Frey, 2006, Statistics Hacks 108-115.
Friedenson, 2005, BRCA1 and BRCA2 Pathways and the Risk of Cancers Other Than Breast or Ovarian, Medscape General Medicine 7(2):60, 28 pages.
Fu, 2010, Repeat subtraction-mediated sequence capture from a complex genome, The Plant Journal, 62:898-909.
Furtado, 2011, Characterization of large genomic deletions in the FBN1 gene using multiplex ligation-dependent probe amplification, BMC Med Gen 12:119-125.
Garber, 2008, Fixing the front end, Nat Biotech 26(10):1101-1104.
Gemayel, 2010, Variable tandem repeats accelerate evolution of coding and regulatory sequences, Ann Rev Genet 44:445-77.
Giusti, 1993, Synthesis and Characterization of f'-Fluorescent-dye-labeled Oligonucleotides, PCR Meth Appl 2:223-227.
Glover, 1995, Sequencing of oligonucleotides using high performance liquid chromatography and electrospray mass spectrometry, Rapid Com Mass Spec 9:897-901.
Gnirke, 2009, Solution hybrid selection with ultra-long oligonucleotides for massively parallel targeted sequencing, nature biotechnology 27:182-9.
Goto, 1994, A Study on Development of a Deductive Object-Oriented Database and Its Application to Genome Analysis, PhD Thesis, Kyushu University, Kyushu, Japan, 106 pages.
Goto, 2010, BioRuby: bioinformatics software for the Ruby programming language, Bioinformatics 26(20):2617-2619.
Green, 2005, Suicide polymerase endonuclease restriction, a novel technique for enhancing PCR amplification of minor DNA template, Appl Env Microbiol 71(8):4721-4727.
Guerrero-Fernandez, 2013, FQbin: a compatible and optimize dformat for storing and managing sequence data, IWBBIO Proceedings, Granada 337-344.
Gupta, 1991, A general method for the synthesis of 3'-sulfhydryl and phosphate group containing oligonucleotides, Nucl Acids Res 19(11):3019-3025.
Gupta, 2014, Expanding the genetic toolkit: ZFNs, TALENs, and CRISPR-Cas9, J Clin Invest 124(10):4154-4161.
Gustincich, 1991, A fast method for high-quality genomic DNA extraction from whole human blood, BioTechniques 11(3):298-302.
Gut, 1995, A procedure for selective DNA alkylation and detection by mass spectrometry, Nucl Acids Res 23(8):1367-1373.
Hallam, 2014, Validation for Clinical Use of, and Initial Clinical Experience with, a Novel Approach to Population-Based Carrier Screening using High-Throughput Next-Generation DNA Sequencing, J Mol Diagn 16:180-9.
Hammond, 1996, Extraction of DNA from preserved animal specimens for use in randomly amplified polymorphic DNA analysis, Anal Biochem 240:298-300.
Hardenbol, 2003, Multiplexed genotyping with sequence-tagged molecular inversion probes, Nat Biotech 21:673-8.
Hardenbol, 2005, Highly multiplexed molecular inversion probe genotyping: over 10,000 targeted SNPs genotyped in a single tube assay, Genome Res 15:269-75.
Harris, 2006, Defects can increase the melting temperature of DNA-nanoparticle assemblies, J Phys Chem B 110(33):16393-6.
Harris, 2008, Helicos True Single Molecule Sequencing (tSMS) Science 320:106-109.
Owens, 1998, Aspects of oligonucleotide and peptide sequencing with MALDI and electrospray mass spectrometry, Bioorg Med Chem 6:1547-1554.
Parameswaran, 2007, A pyrosequencing-tailored nucleotide barcode design unveils opportunities for large-scale sample multiplexing, Nucl Acids Rese 35:e130, 27 pages.
Parkinson, 2012, Preparation of high-quality next-generation sequencing libraries from picogram quantities of target DNA, Genome Res 22:125-133.
Pastor, 2010, Conceptual modeling of human genome mutations: a dichotomy between what we have and what we shoudl have, 2010 Proc BIOSTEC Bioinformatics, pp. 160-166.
Paton, 2000, Conceptual modelling of genomic information, Bioinformatics 16(6):548-57.

(56) References Cited

OTHER PUBLICATIONS

Pearson, 1988, Improved tools for biological sequence comparison, PNAS 85(8):2444-8.
Pertea, 2003, TIGR gene indices clustering tools (TGICL), Bioinformatics 19(5):651-52.
Pieles, 1993, Matrix-assisted laser desorption ionization time-of-flight mass spectrometry: A powerful tool for the mass and sequence analysis of natural and modified oligonucleotides, Nucleic Acids Res 21:3191-3196.
Pinho, 2013, MFCompress: a compression tool for FASTA and multi-FASTA data, Bioinformatics 30(1):117-8.
Porreca, 2007, Multiplex amplificaiton of large sets of human exons, Nat Meth 4(11):931-936.
Porreca, 2013, Analytical performance of a Next-Generation DNA sequencing-based clinical workflow for genetic carrier screening, American Society of Human Genetics 63rd Annual Meeting, Abstract, Oct. 22, 2013, 2 pages.
Pourmand, 2006, PathgoenMIPer: a tool for the design of molecular inversion probes, BMC informatics 7:500, 10 pages.
Procter, 2006, Molecular diagnosis of Prader-Willi and Angelman syndromes by methylation-specific melting analysis and methylation-specific multiplex ligation-dependent probe amplification, Clin Chem 52(7):1276-83.
Qiagen, 2011, Gentra Puregene handbook, 3d Ed., 72 pages.
Quail, 2010, DNA: Mechanical Breakage, in Encyclopedia of Life Sciences, John Wiley & Sons Ltd, Chicester (5 pages).
Rambaut, 1997, Seq-Gen:an application for the Monte Carlo simulation of DNA sequence evolution along phylogenetic trees, Bioinformatics 13:235-38.
Richards, 2008 ACMG recommendations for standards for interpretation and reporting of sequence variations: Revisions, Genet Med 10(4):294-300.
Richter, 2008, MetaSim—A Sequencing Simulator for Genomics and Metagenomics, PLoS One 3:e3373, 12 pages.
Roberts, 1980, Restriction and modification enzymes and their recognition sequences, Nucleic Acids Res 8(1):r63-r80.
Rodriguez, 2010, Constructions from Dots and Lines, Bull Am Soc Inf Sci Tech 36(6):35-41.
Rosendahl, 2013, CFTR, SPINK1, CTRC and PRSS1 variants in chronic pancreatitis: is the role of mutated CFTR overestimated?, Gut 62:582-592.
Rothberg, 2011, An integrated semiconductor device enabling non-optical genome sequencing, Nature 475:348-352.
Rowntree, 2003, The phenotypic consequences of CFTR mutations, Ann Hum Gen 67:471-485.
Saihan, 2009, Update on Usher syndrome, Curr Op Neurology 22(1):19-24.
Sanger, 1977, DNA Sequencing with chain-terminating inhibitors, PNAS 74(12):5463-5467.
Santa Lucia, 1998, A unified view of polymer, dumbbell, and oligonucleotide DNA nearest-neighbor thermodynamics, PNAS 95(4):1460-5.
Sargent, 1987, Isolation of differentially expressed genes, Meth Enzym 152:423-432.
Sauro, 2004, How Do You Calculate a Z-Score/ Sigma Level?, https://www.measuringusability.com/zcalc.htm (online publication), 3 pages.
Sauro, 2004, What's a Z-score and Why Use It in Usability Testing?, https://www.measuringusability.com/z.htm (online publication), 4 pages.
Schadt, 2010, A window into third-generation sequencing, Human Mol Genet 19(R2):R227-40.
Schatz, 2010, Assembly of large genomes using second-generation sequencing, Genome Res., 20:1165-1173.
Schiffman, 2007, Adapting molecular inversion probe (MIP) technology for allele quantification in childhood leukemia, Journal of Clinical Oncology, 25, p. 530, 5 pages.
Schiffman, 2009, Molecular inversion probes reveal patterns of 9p21 deletion and copy number aberrations in childhood leukemia, Cancer Genetics and Cytogenetics 193:9-18.
Schneeberger, 2011, Reference-guided assembly of four diverse *Arabidopsis thaliana* genomes, PNAS 108 (25):10249-10254.
Schouten, 2002, Relative Quantification of 40 Nucleic Acid Sequences by Multiplex Ligation-Dependent Probe Amplification, Nucle Acids Res 30 (12):257, 13 pages.
Schrijver, 2005, Diagnostic testing by CFTR gene mutation analysis in a large group of Hispanics, J Mol Diag 7(2):289-299.
Schuette, 1995, Sequence analysis of phosphorothioate oligonucleotides via matrix-assisted laser desorption ionization time-of-flight mass spectrometry, J Pharm Biomed Anal 13:1195-1203.
Schwartz, 2009, Identification of cystic fibrosis variants by polymerase chain reaction/oligonucleotide ligation assay, J Mol Diag 11(3):211-15.
Schwartz, 2011, Clinical utility of single nucleotide polymorphism arrays, Clin Lab Med 31(4):581-94.
Sequeira, 1997, Implementing generic, object-oriented models in biology, Ecological Modeling 94.1:17-31.
Shagin, 2002, A novel method for SNP detection, Genome Res 12:1935-1942.
Shen, 2011, High quality DNA sequence capture of 524 disease candidate genes, PNAS 108(16):6549-6554.
Shen, 2013, Multiplex capture with double-stranded DNA probes, Genome Medicine 5(50):1-8.
Sievers, 2011, Fast, scalable generation of high-quality protein multiple sequence alignments using Clustal Omega, Mol Syst Biol 7:539, 6 pages.
Simpson, 2009, ABySS: A parallel assembler for short read sequence data, Genome Res., 19(6):1117-23.
Slater, 2005, Automated generation of heuristics for biological sequence comparison, BMC Bioinformatics 6:31, 11 pages.
Smirnov, 1996, Sequencing oligonucleotides by exonuclease digestion and delayed extraction matrix-assisted laser desorption ionization time-of-flight mass spectrometry, Anal Biochem 238:19-25.
Smith, 1985, The synthesis of oligonucleotides containing an aliphatic amino group at the 5' terminus: synthesis of fluorescent DNA primers for use in DNA sequence analysis, Nucl Acid Res 13:2399-2412.
Smith, 2010, Highly-multiplexed barcode sequencing: an efficient method for parallel analysis of pooled samples, Nucleic Acids Research 38(13):e142, 8 pages.
Soni, 2007, Progress toward ultrafast DNA sequencing using solid-state nanopores, Clin Chem 53(11):1996-2001.
Binladen J., et al., "The Use of Coded PCR Primers Enables High-throughput Sequencing of Multiple Homolog Amplification Products by 454 Parallel Sequencing," PLoS One, Feb. 2007, vol. 2 (2), Article No. e197, 9 Pages, XP002482385.
Lank S.M., et al., "A Novel Single cDNA Amplicon Pyrosequencing Method for High-Throughput, Cost-Effective Sequence-Based HLA class I Genotyping. Supplemental Tables 1-7," Human Immunology, Jul. 30, 2010, pp. 1011-1017, XP055206965, 19 total pages.

Pair of barcodes:

①

②

③

④

METHODS FOR MAINTAINING THE INTEGRITY AND IDENTIFICATION OF A NUCLEIC ACID TEMPLATE IN A MULTIPLEX SEQUENCING REACTION

RELATED APPLICATIONS

The present application is a continuation application of U.S. patent application Ser. No. 17/149,504, filed Jan. 14, 2021, which is a continuation of U.S. patent application Ser. No. 14/854,629, filed Sep. 15, 2015, which is a divisional application of U.S. patent application Ser. No. 13/081,660, filed Apr. 7, 2011, which claims the benefit of and priority to U.S. provisional patent application Ser. No. 61/426,817, filed Dec. 23, 2010, the contents of each of which are incorporated by reference herein in their entirety.

FIELD OF THE INVENTION

The invention generally relates to methods for maintaining the integrity and identification of a nucleic acid template in a multiplex sequencing reaction.

BACKGROUND

Sequencing-by-synthesis involves template-dependent addition of nucleotides to a template/primer duplex. Nucleotide addition is mediated by a polymerase enzyme and added nucleotides may be labeled in order to facilitate their detection. Single molecule sequencing has been used to obtain high-throughput sequence information on individual DNA or RNA. The ability to multiplex samples, i.e., pool different patient samples, is important for decreasing costs and increasing the through-put of sequencing-by-synthesis platforms.

One issue that presents itself in a multiplex sequencing reaction is maintaining accurate identification of a sample throughout the sequencing process. Unfortunately, the sample preparation phase frequently introduces errors into the subsequent sequencing reaction. For example, template molecules may physically overlap on a substrate; and in some cases result in a detectable erroneous signal. In any sequencing process that requires high accuracy, such errors can have a significant impact on results. Next generation sequencing typically involves the generation of an in vitro library; arraying of nucleic acid templates into physically distinct locations on a solid support (and optional clonal amplification of the templates into spatially localized clusters); and the sequencing-by-synthesis reaction itself. Errors can occur during generation of the library, arraying and amplification steps that result in molecular overlap of different patient samples. For example, heteroduplexes, i.e., improper pairing of template strands from different samples, may form during the amplification of the multiplexed samples. Molecular overlap during any of the first three steps in the process may lead to assigning sequencing data to the wrong patient sample. Other errors can be introduced due to incomplete amplification, stray labeled primers, and other sources that result in erroneous signal detection. In a single molecule sequencing protocol, such errors can have a significant affect on the results. Accordingly, methods for reducing or eliminating errors in such procedures are needed.

SUMMARY

The invention generally provides methods for validating the results of a molecular detection assay and for enabling the detection of errors introduced in sample preparation. The invention is applicable to nucleic acid sequencing, protein detection, and other methods that involve precise measurement of the presence and/or amount of an analyte. The invention utilizes two or more identifiers that are uniquely associated with an analyte of interest, such that the identifiers will only be present when the analyte of interest is detected. In this way, false positive and/or false negative results are avoided by requiring concomitant detection of two or more independent markers associated with the analyte to be detected.

The invention is especially useful in multiplex next-generation sequencing applications in which errors can have a significant impact on results, but is also applicable across a broad range of detection assays, including protein detection assays. The invention is based upon using two or more identifiers, such as nucleic acid barcodes that are uniquely associated with an analyte to be detected. For example, in sequencing applications, a pair of barcodes are placed such that they flank the sequence of interest. The identifiers are unique to the sample, so that valid sequence data are confirmed by the presence of the pair of flanking identifiers. In contrast, template containing only one identifier or an incorrect pair (i.e., a pair or more of identifiers not associated with the same template) will be excluded from analysis. Thus, methods of the invention make it possible to determine whether the integrity of a sample was maintained during a multiplex sequencing reaction, and prevent the assigning of sequence data to the wrong sample.

In other applications, two or more nucleic acid tags are associated with a protein or other analyte of interest. Identification of the sequence tags confirms the accuracy of the detection of the protein. In this embodiment of the invention, a protein is captured by a binding agent, such as an antibody, that is coupled to at least two oligonucleotides of known sequence. The identification of the captured protein is confirmed via sequencing of the tags that are uniquely associated with the binding agent. The presence of both sequence tags validates the capture of the target protein.

In protein detection, identifiers can also include detectable labels, antibodies, other proteins, including glycoproteins, vitamins, steroids, viral particles, and the like that bind specifically to a protein of interest. Detection of the identifiers validates that the protein of interest has been found.

In nucleic acid sequencing, preferred identifiers are nucleic acid barcodes. The barcodes can be of any appropriate length (e.g., from about 2 to about 50 nucleotides) and any number of barcode sequences can be used. Preferably, the barcodes are present in pairs that flank the template to be sequenced, or portions thereof. While the pair of barcodes associated with any given template is unique, individual barcode sequences can be used with multiple templates as long as no pair is used across two different samples. While it is possible, and may be preferred in some circumstances, to use more than two barcoded sequences or other identifiers, the invention will be exemplified using pairs of identifier molecules. In a preferred configuration, each template from a particular sample is associated with the same unique pair of barcode sequences. The pairs ideally flank the region of the template that is to be sequenced. Thus, the pairs can be contiguous with a region of interest or can be separated from the region of interest by spacers (which include intervening sequence in the template or inserted spacer sequence) or by naturally-occurring sequence. Other identifiers, such as nucleic acid binding proteins, optical labels, nucleotide analogs, and others known in the art can be used as identifiers according to the invention.

In certain aspects, methods of the invention involve obtaining a template nucleic acid, incorporating a pair of sequence identifiers into the template, and sequencing the template. Methods of the invention may further include directly or indirectly attaching the template to a substrate. The template may be amplified prior to attachment to the substrate or may be amplified on the substrate after it has been attached to the substrate. In particular embodiments, the template is amplified after it has been attached to the substrate. In other embodiments, the template is amplified before being attached to the substrate and is also subsequently amplified after it has been attached to the substrate.

Identifiers can be incorporated anywhere on a template. For example, a first identifier can be incorporated into a 5' end of the template and a second identifier can incorporated into a 3' end of the template. The first and second identifiers are designed such that each set of identifiers is correlated to a particular sample (e.g., material obtained from a particular patient or group of patients), allowing samples to be distinguished and/or validated. The first and second identifiers may be the same or different, so long as the combination is unique with respect to the sample or sub-sample that one seeks to distinguish and/or validate.

After identifiers have been incorporated into the template, the template is sequenced. Sequencing may be by any method known in the art. Sequencing-by-synthesis is a common technique used in next generation procedures and works well with the instant invention. However, other sequencing methods can be used, including sequence-by-ligation, sequencing-by-hybridization; gel-based techniques and others. In general, sequencing involves hybridizing a primer to a template to form a template/primer duplex, contacting the duplex with a polymerase in the presence of a detectably-labeled nucleotides under conditions that permit the polymerase to add nucleotides to the primer in a template-dependent manner. Signal from the detectable label is then used to identify the incorporated base and the steps are sequentially repeated in order to determine the linear order of nucleotides in the template. Exemplary detectable labels include radiolabels, florescent labels, enzymatic labels, etc. In particular embodiments, the detectable label may be an optically detectable label, such as a fluorescent label. Exemplary fluorescent labels include cyanine, rhodamine, fluorescein, coumarin, BODIPY, alexa, or conjugated multi-dyes.

Numerous techniques are known for detecting sequence and for identifying barcodes and some are exemplified below. However, the exact means for detecting and compiling sequence data does not affect the function of the invention described herein.

If the analyte to be detected is not a nucleic acid, the identifiers can still be nucleic acid barcodes that are associated with the analyte binding moiety. Sequencing of the barcodes then validates detection of the analyte (i.e., the presence of two or more barcodes in association with the binder must be detected in order to validate the detection). In protein detection, the identifiers can also be part of the primary structure of the protein to be detected. In this embodiment, the amino acid sequence of the protein is determined (e.g., by mass spectrometry or Edman degradation). The embedded amino acid sequence identifiers would have to be present in the amino acid sequence in order to validate the identity of the protein.

DETAILED DESCRIPTION

Methods of the invention relate to validating and maintaining the integrity of a nucleic acid template in a multiplex sequencing reaction. Methods of the invention involve obtaining a template nucleic acid, incorporating a pair of sequence identifiers into the template, and sequencing the template.

Figure 1:
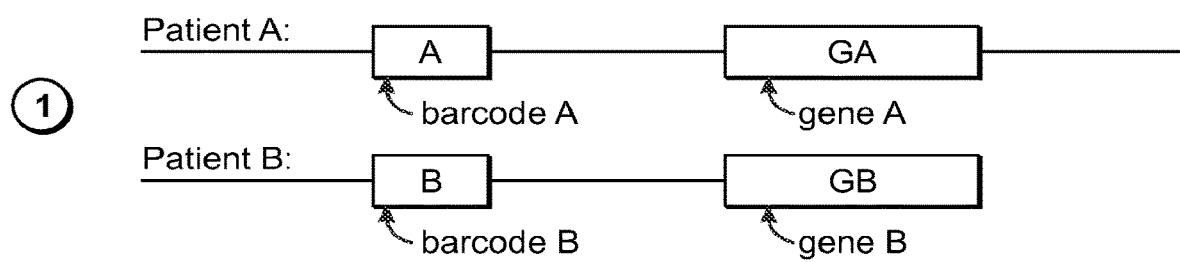
FIG. 1 is a set of drawings showing how molecular overlap can lead to apparent high quality, but incorrect sequence data.
Figure 1:
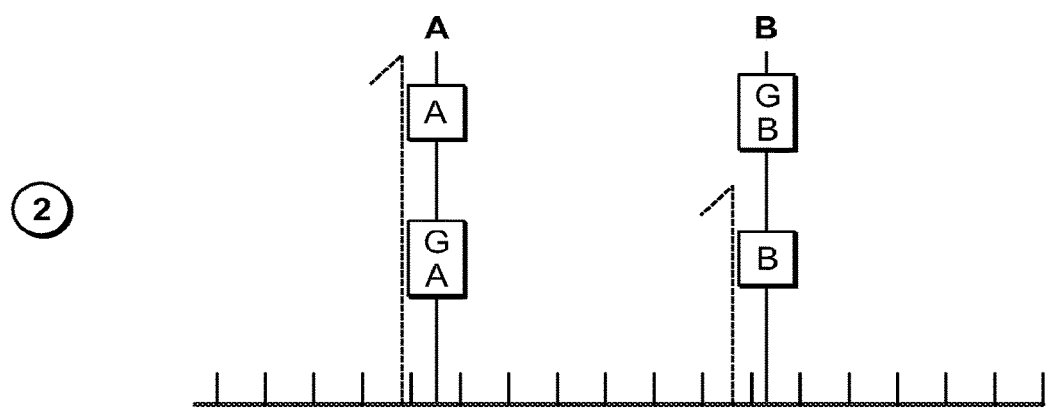
Figure 1:
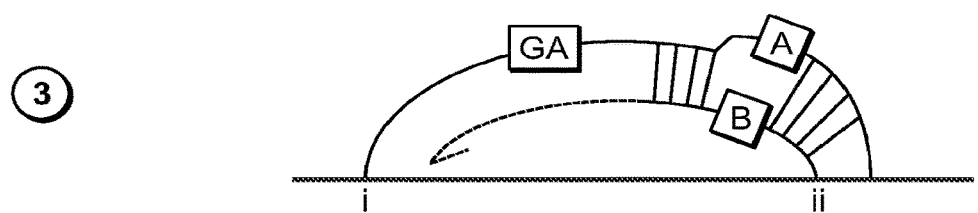
Figure 1:
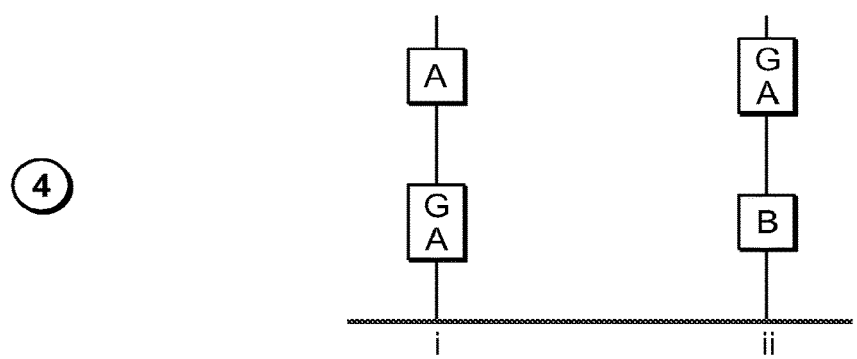

Reference is now made to FIG. 1, which shows a set of drawings depicting one example of how molecular overlap can lead to apparent high quality, but incorrect sequence data. Panel 1 shows the pooling of nucleic acid libraries from two patient samples, A and B. Each template has a gene fragment from that patient (e.g., GA), and a molecular barcode specific to that patient (e.g., A). As shown in panel 1, nucleic acids from patient A's sample include a barcode A and a gene fragment GA, and nucleic acids from patient B's sample include nucleic a barcode B and a gene fragment GB.

Panel 2 shows that after pooling, the samples are then hybridized to primers at discrete locations on a flow cell. In this figure, the nucleic acid from patient A and the nucleic acid from patient B land within a cluster radius on the solid support. When the amplification process begins, primers attached to the solid support extend on each template. In one case (patient A's nucleic acid template), the primer extends across a full length of the template. In the other case (patient B's nucleic acid template), the primer partially extends, incorporating the sequence of barcode B and common priming sequence, but not the gene fragment sequence GB from patient B's nucleic acid template.

Panel 3 shows an example of improper molecular overlap. After extension, the duplexes are denatured and re-annealed for another amplification cycle. This example shows improper molecular overlap via formation of a heteroduplex between patient A's nucleic acid template and patient B's nucleic acid template. In this example, strand i hybridizes to strand ii, forming a bridge. Barcode regions of each strand are not complementary, but the strands still hybridize because of the amount of common priming sequence on both sides of the barcode. Consequently, a polymerase will extend strand ii, copying patient A's gene fragment onto a strand containing patient B's barcode. A chimeric molecule has been formed.

Panel 4 shows the results of this molecular overlap. Strand ii contains the barcode for patient B but the gene fragment for patient A. During the sequencing process, patient A's sequence data will be improperly and incorrectly associated with patient B. If the chimeric molecule is formed early in the amplification process, it can dominate the cluster of amplification products, leading to a homogenous clonal chimeric cluster. During sequencing, this would give a high-quality signal, but the data will be assigned to the wrong sample because it has become associated with the wrong barcode.

Figure 2:
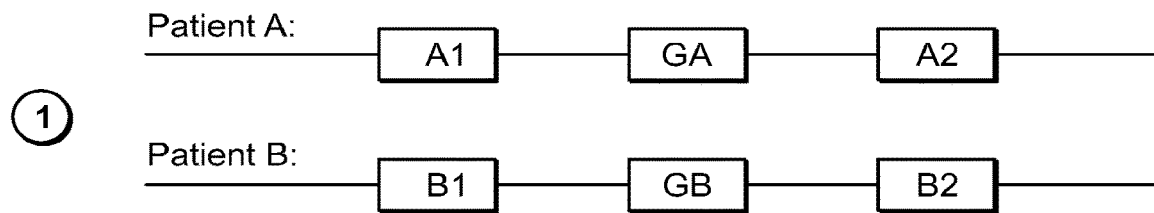
FIG. 2 is a set of drawings depicting how methods of the invention allow one to detect, during analysis, whether the integrity of a patient's sample was maintained during a multiplex sequencing reaction.
Figure 2:
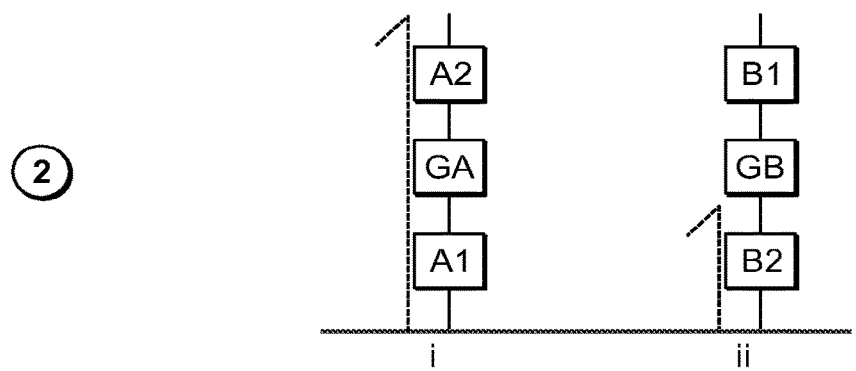
Figure 2:
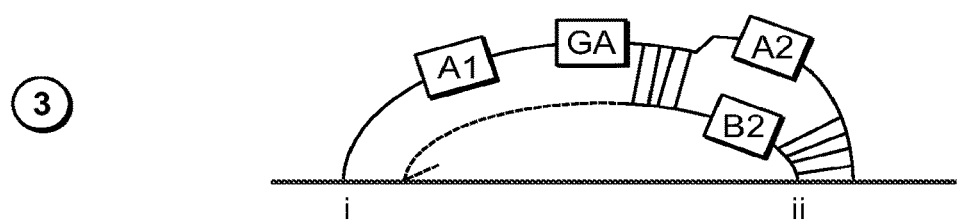
Figure 2:
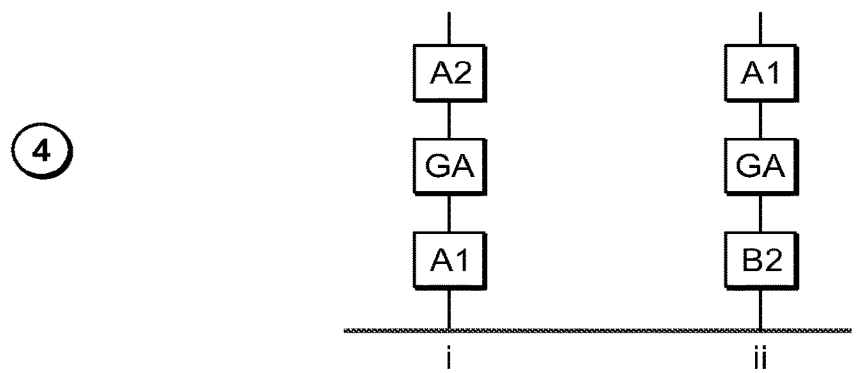

Reference is now made to FIG. 2, which shows a set of drawings depicting how methods of the invention allow one to detect, during analysis, whether the integrity of a patient's sample was maintained during a multiplex sequencing reaction. Panel 1 shows the pooling of nucleic acid libraries from two patient samples, A and B. Each template has a gene fragment from that patient (e.g., GA), and a pair of sequence identifiers (first and second) specific to that patient (e.g., A1 and A2).

The first and second identifiers are designed such that each set of identifiers is correlated to a particular patient, allowing patient samples to be distinguished. The first and second identifiers may be the same. Alternatively, the first and second identifiers may be different. In certain embodiments, the pair of identifiers are first and second barcode sequences that are attached to the template. The barcode sequences may be attached to the template such that a first barcode sequence is attached to a 5' end of the template and a second barcode sequence is attached to a 3' end of the template. The first and second barcode sequences may be the same, or they may be different.

In this figure, the sequence identifiers are pairs of barcode sequences. This figure also shows that the pair of barcode sequences are attached to the nucleic acid template at the 5' and the 3' ends of the template, such that the barcode sequences flank the gene fragment of each template. As shown in panel 1, the pool includes patient A's sample which is nucleic acid templates having barcode sequences A1 and A2 that flank gene fragment GA, and also includes patient B's sample which is nucleic acid templates having barcode sequences B1 and B2 and gene fragment GB.

Panel 2 shows that after pooling, the samples are then hybridized to primers at discrete locations on a flow cell. In this figure, the nucleic acid from patient A and the nucleic acid from patient B land within a cluster radius on the solid support. When the amplification process begins, primers attached to the solid support extend on each template. In one case (patient A's nucleic acid template), the primer extends across a full length of the template. In the other case (patient B's nucleic acid template), the primer partially extends, incorporating the sequence of barcode B2 and common priming sequence, but not the gene fragment sequence GB from patient B's nucleic acid template or the sequence of barcode B1.

Panel 3 shows an example of improper molecular overlap. After extension, the duplexes are denatured and re-annealed for another amplification cycle. This example shows improper molecular overlap via formation of a heteroduplex between patient A's nucleic acid template and patient B's nucleic acid template. In this example, strand i hybridizes to strand ii, forming a bridge. Barcode regions A2 and B2 of each strand are not complementary, but the strands still hybridize because of the amount of common priming sequence on both sides of the barcode. Consequently, a polymerase will extend strand ii, copying patient A's gene fragment. However, in the case of two barcodes, only one of patient B's barcodes (B2) will be contained in the copied strand. The other barcode will be one of patient A's barcode sequences (A1). Unlike the example in FIG. 1, the chimeric molecule formed in this example includes one barcode sequence from patient A (A1) and one barcode sequence from patient B (B2).

Panel 4 shows the results of this molecular overlap. While strand ii contains the gene fragment for patient A, it contains only one of patient B's barcodes (B2). The other barcode will be one of patient A's barcode sequences (A1). While each barcode sequence on its own is a valid barcode sequence, taken together, the two barcode sequences do not form a valid barcode sequence pair. During the sequencing process, this would yield a high-quality signal, but during data analysis the molecules would be recognized as invalid because the data contains an invalid barcode sequence pair, i.e., it is known that barcode sequence A1 should not be seen together with barcode sequence B2 and hence a crossover has occurred. Thus during analysis, it is determined that the integrity of the patient's sample was not maintained and the data can then be excluded from final analysis.

Figure 3:
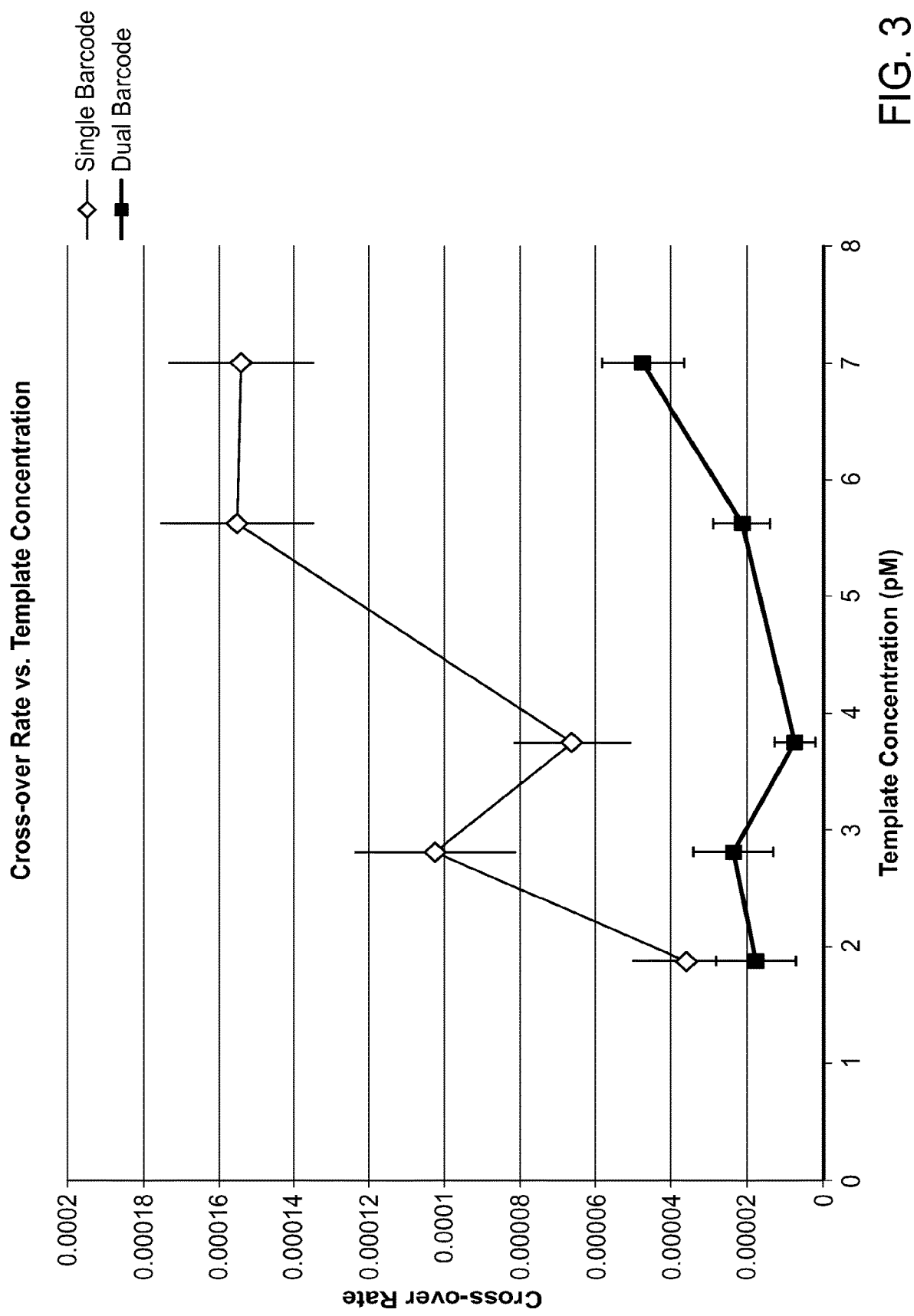
FIG. 3 is a graph showing that methods of the invention dramatically reduce false positives in a multiplex sequencing reaction.

FIG. 3 is a graph showing that methods of the invention dramatically reduce false positives in a multiplex sequencing reaction. Two sample preparation procedures were performed prior to conducting a sequencing reaction as described herein. In the first sample preparation, only a single barcode sequence was attached to template molecules from different samples prior to pooling and then sequencing. In the second sample preparation, two barcode sequences were attached to template molecules from different samples prior to pooling and then sequencing.

Data in FIG. 3 show that with use of only a single barcode sequence per template molecule, molecular overlap can lead to apparent high quality, but incorrect sequence data (diamond points). A single barcode sequence was attached to nucleic acids from sample A and a different single barcode sequence was attached to nucleic acids from sample B. The barcoded templates from each sample (A and B) were then pooled. After pooling, the samples were then hybridized to primers at discrete locations on a flow cell. Without being limited by any particular theory or mechanism of action, the data in FIG. 3 suggest that the nucleic acid from sample A and the nucleic acid from sample B landed within a cluster radius on the solid support. When the amplification process began, primers attached to the solid support extended on each template. In some instances, the primer partially extended, incorporating the sequence of barcode B and common priming sequence, but not the gene fragment sequence of sample B.

After extension, the duplexes were denatured and re-annealed for another amplification cycle. In certain cases, a heteroduplex between sample A's nucleic acid template and sample B's nucleic acid template was formed. The barcode regions of each strand were not complementary, but the strands still hybridized because of the amount of common priming sequence on both sides of the barcode. Consequently, a polymerase extended the strand copying sample A's gene fragment onto a strand containing sample B's barcode. A chimeric molecule was formed. During the sequencing process, sample A's sequence data improperly and incorrectly associated with sample B. Since the chimeric molecule was formed early in the amplification process, it dominated the cluster of amplification products, leading to a homogenous clonal chimeric cluster. During sequencing, this gave a high-quality signal, but the data was assigned to the wrong sample because it had become associated with the wrong barcode. See FIG. 3, diamond points.

FIG. 3 also provides data showing that methods of the invention dramatically reduce false positives in a multiplex sequencing reaction (square points). A pair of barcode sequences (A1 and A2 and B1 and B2) were attached to nucleic acids from two different samples, samples A and B. The pair of barcode sequences were attached to the nucleic acid templates at the 5' and the 3' ends of each template, such that the barcode sequences flanked the gene fragment of each template.

The barcoded templates from each sample (A and B) were then pooled. After pooling, the samples were then hybridized to primers at discrete locations on a flow cell. Without being limited by any particular theory or mechanism of action, the data in FIG. 3 suggest that the nucleic acid from sample A and the nucleic acid from sample B landed within a cluster radius on the solid support. When the amplification process began, primers attached to the solid support extended on each template. In certain instances, the primer partially extended, incorporating the sequence of barcode B2 and common priming sequence, but not the gene fragment sequence from sample B's nucleic acid template or the sequence of barcode B1.

After extension, the duplexes were denatured and re-annealed for another amplification cycle. In this example, template from sample A and template from sample B hybridized, forming a bridge. Barcode regions A2 and B2 of each strand were not complementary, but the strands still hybridized because of the amount of common priming sequence on both sides of the barcode. Consequently, a polymerase extended the strand, copying sample A's gene fragment. However, in the case of two barcodes, only one of sample B's barcodes (B2) was contained in the copied strand. The other barcode was one of sample A's barcode sequences (A1). Unlike the single barcode amplification reaction, the chimeric molecule formed in this amplification reaction included one barcode sequence from sample A (A1) and one barcode sequence from sample B (B2).

While each barcode sequence on its own was a valid barcode sequence, taken together, the two barcode sequences did not form a valid barcode sequence pair. During the sequencing process, this yielded a high-quality signal, but during data analysis the molecules were recognized as invalid because the data contained an invalid barcode sequence pair, i.e., it was known that barcode sequence A1 should not be seen together with barcode sequence B2 and hence a crossover has occurred. Thus during analysis, it was determined that the integrity of the patient's sample was not maintained and the data was excluded from final analysis (square points in FIG. 3). Thus, data herein show that methods of the invention dramatically reduce crossover rate. High crossover rate makes it more likely that false positives and/or false negatives will occur.

The following sections discuss general considerations for barcode sequences, attaching barcode sequences to nucleic acid templates, and nucleic acid sequencing, for example, template considerations, polymerases useful in sequencing-by-synthesis, choice of surfaces, reaction conditions, signal detection and analysis.

Nucleic Acid Templates

Nucleic acid templates include deoxyribonucleic acid (DNA) and/or ribonucleic acid (RNA). Nucleic acid templates can be synthetic or derived from naturally occurring sources, or may include both synthetic and natural sequence; and may include PCR product. In one embodiment, nucleic acid template molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present invention include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA.

Nucleic acid obtained from biological samples typically is fragmented to produce suitable fragments for analysis. In one embodiment, nucleic acid from a biological sample is fragmented by sonication. Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Generally, individual nucleic acid template molecules can be from about 1 base to about 20 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-$C_6H_4$—$(OCH_2$—$CH_2)_xOH$, x=9-10, Triton® X-100R, Triton® X-114 x=7-8), octyl glucoside, polyoxyethylene(9) dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 34(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), .beta.-mercaptoethanol, DTE, GSH, cysteine, cysteamine, tricarboxyethyl phosphine (TCEP), or salts of sulfurous acid.

Barcode Sequences

In certain embodiments, the sequence identifiers are barcode sequences that are attached to or incorporated into a nucleic acid template. The barcode sequences may be attached to the template such that a first barcode sequence is attached to a 5' end of the template and a second barcode sequence is attached to a 3' end of the template. The first and second barcode sequences may be the same, or they may be different. Barcode sequence may be incorporated into a contiguous region of a template that includes the target to be sequenced.

Exemplary methods for designing sets of barcode sequences and other methods for attaching barcode sequences are shown in U.S. Pat. Nos. 6,138,077; 6,352,828;

5,636,400; 6,172,214; 6235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety.

The barcode sequence generally includes certain features that make the sequence useful in sequencing reactions. For example the barcode sequences can be designed to have minimal or no homopolymer regions, i.e., 2 or more of the same base in a row such as AA or CCC, within the barcode sequence. The barcode sequences can also be designed so that they do not overlap the target region to be sequence or contain a sequence that is identical to the target.

The first and second barcode sequences are designed such that each pair of sequences is correlated to a particular sample, allowing samples to be distinguished and validated. Methods of designing sets of barcode sequences is shown for example in Brenner et al. (U.S. Pat. No. 6,235,475), the contents of which are incorporated by reference herein in their entirety. In certain embodiments, the barcode sequences range from about 2 nucleotides to about 50; and preferably from about 4 to about 20 nucleotides. Since the barcode sequence is sequenced along with the template nucleic acid or may be sequenced in a separate read, the oligonucleotide length should be of minimal length so as to permit the longest read from the template nucleic acid attached. Generally, the barcode sequences are spaced from the template nucleic acid molecule by at least one base.

Methods of the invention involve attaching the barcode sequences to the template nucleic acids. Template nucleic acids are able to be fragmented or sheared to desired length, e.g. generally from 100 to 500 bases or longer, using a variety of mechanical, chemical and/or enzymatic methods. DNA may be randomly sheared via sonication, exposed to a DNase or one or more restriction enzymes, a transposase, or nicking enzyme. RNA may be fragmented by brief exposure to an RNase, heat plus magnesium, or by shearing. The RNA may be converted to cDNA before or after fragmentation.

Barcode sequence is integrated with template using methods known in the art. Barcode sequence is integrated with template using, for example, a ligase, a polymerase, Topo cloning (e.g., Invitrogen's topoisomerase vector cloning system using a topoisomerase enzyme), or chemical ligation or conjugation. The ligase may be any enzyme capable of ligating an oligonucleotide (RNA or DNA) to the template nucleic acid molecule. Suitable ligases include T4 DNA ligase and T4 RNA ligase (such ligases are available commercially, from New England Biolabs). Methods for using ligases are well known in the art. The polymerase may be any enzyme capable of adding nucleotides to the 3' and the 5' terminus of template nucleic acid molecules. Barcode sequence can be incorporated via a PCR reaction as part of the PCR primer.

The ligation may be blunt ended or via use of over hanging ends. In certain embodiments, following fragmentation, the ends of the fragments may be repaired, trimmed (e.g. using an exonuclease), or filled (e.g., using a polymerase and dNTPs), to form blunt ends. Upon generating blunt ends, the ends may be treated with a polymerase and dATP to form a template independent addition to the 3'-end and the 5-end of the fragments, thus producing a single A overhanging. This single A is used to guide ligation of fragments with a single T overhanging from the 5'-end in a method referred to as T-A cloning.

Alternatively, because the possible combination of overhangs left by the restriction enzymes are known after a restriction digestion, the ends may be left as is, i.e., ragged ends. In certain embodiments double stranded oligonucleotides with complementary over hanging ends are used.

Surface Attachment

Methods of the invention may involve attaching or immobilizing barcoded nucleic acid templates to solid supports. Such methods are described for example in Sabot et al. (U.S. patent application number 2009/0226975), Adessi et al. (U.S. Pat. No. 7,115,400), and Kawashima et al. (U.S. patent application number 2005/0100900), the content of each of which is incorporated by reference herein in its entirety.

The term immobilized as used herein is intended to encompass direct or indirect attachment to a solid support via covalent or non-covalent bond(s). In certain embodiments of the invention, covalent attachment may be used, but generally all that is required is that template remain immobilized on the support. Typically oligonucleotides are immobilized such that a 3' end is available for enzymatic extension and at least a portion of the sequence is capable of hybridizing to a complementary sequence. Immobilization can occur via hybridization to a surface attached oligonucleotide. Alternatively, immobilization can occur by means other than base-pairing hybridization, such as the covalent attachment set forth above.

Substrates or supports for use in the invention include, but are not limited to, latex beads, dextran beads, polystyrene surfaces, polypropylene surfaces, polyacrylamide gel, gold surfaces, glass surfaces and silicon wafers. In certain embodiments, the solid support may include an inert substrate or matrix that has been functionalized, for example by the application of a layer or coating of an intermediate material including reactive groups that permit covalent attachment to molecules such as polynucleotides.

Amplification

In certain embodiments, methods of the invention involve amplifying barcoded nucleic acid templates prior to sequencing the templates. Such methods are described for example in Sabot et al. (U.S. patent application number 2009/0226975), Adessi et al. (U.S. Pat. No. 7,115,400), and Kawashima et al. (U.S. patent application number 2005/0100900), the content of each of which is incorporated by reference herein in its entirety.

Primer oligonucleotides or amplification sequences are polynucleotide sequences that are capable of annealing specifically to a single stranded polynucleotide sequence to be amplified under conditions encountered in a primer annealing step of an amplification reaction. Generally, the terms nucleic acid, polynucleotide and oligonucleotide are used interchangeably herein. The different terms are not intended to denote any particular difference in size, sequence, or other property unless specifically indicated otherwise. For clarity of description the terms may be used to distinguish one species of molecule from another when describing a particular method or composition that includes several molecular species.

Primers may additionally include non-nucleotide chemical modifications, for example to facilitate covalent attachment of the primer to a solid support. Certain chemical modifications may themselves improve the function of the molecule as a primer or may provide some other useful functionality, such as providing a cleavage site that enables the primer (or an extended polynucleotide strand derived therefrom) to be cleaved from a solid support. Useful chemical modifications can also provide reversible modifications that prevent hybridization or extension of the primer until the modification is removed or reversed. Similarly, other molecules attached to a surface in accordance with the invention can include cleavable linker moieties and or reversible modifications that alter a particular chemical activity of function of the molecule.

A plurality of oligonucleotides used in the methods set forth herein can include species that function as capture oligonucleotides. The capture oligonucleotides may include a template specific portion, namely a sequence of nucleotides capable of annealing to a primer binding sequence in a single stranded polynucleotide molecule of interest such as one that is to be amplified. The primer binding sequences will generally be of known sequence and will therefore be complementary to a region of known sequence of the single stranded polynucleotide molecule. The capture oligonucleotides may include a capture sequence and an amplification sequence. For example, a capture oligonucleotide may be of greater length than amplification primers that are attached to the same substrate, in which case the 5' end of the capture sequences may comprise a region with the same sequence as one of the amplification primers. A portion of a template, such as the 3' end of the template, may be complementary to the 3' of the capture sequences. The 5' end of the template may contain a region that comprises a sequence identical to one of the amplification primers such that upon copying the template, the copy can hybridize to the immobilized amplification primer. Thus, an oligonucleotide species that is useful in the methods set forth herein can have a capture sequence, an amplification sequence or both. Conversely, an oligonucleotide species can lack a capture sequence, an amplification sequence or both. In this way the hybridization specificity of an oligonucleotide species can be tailored for a particular application of the methods.

The length of primer binding sequences need not be the same as those of known sequences of polynucleotide template molecules and may be shorter, being particularly 16-50 nucleotides, more particularly 16-40 nucleotides and yet more particularly 20-30 nucleotides in length. The desired length of the primer oligonucleotides will depend upon a number of factors. However, the primers are typically long (complex) enough so that the likelihood of annealing to sequences other than the primer binding sequence is very low. Accordingly, known sequences that flank a template sequence can include a primer binding portion and other portions such as a capture sequence, barcode sequence or combination thereof.

In certain embodiments of the invention, amplification primers for solid phase amplification are immobilized by covalent attachment to the solid support at or near the 5' end of the primer, such that a portion of the primer is free to anneal to its cognate template and the 3' hydroxyl group is free to function in primer extension.

The chosen attachment chemistry will typically depend on the nature of the solid support and any functionalization or derivatization applied to it. In the case of nucleic acid embodiments, the primer itself may include a moiety which may be a non-nucleotide chemical modification to facilitate attachment. For example, the primer may include a sulfur containing nucleophile such as a phosphorothioate or thiophosphate at the 5' end. In the case of solid supported polyacrylamide hydrogels, this nucleophile may bind to a bromoacetamide group present in the hydrogel. In one embodiment, the means of attaching primers to the solid support is via St phosphorothioate attachment to a hydrogel comprised of polymerized acrylamide and N-(5-bromoacetamidylpentyl) acrylamide (BRAPA).

A uniform, homogeneously distributed lawn of immobilized oligonucleotides may be formed by coupling (grafting) a solution of oligonucleotide species onto the solid support. The solution can contain a homogenous population of oligonucleotides but will typically contain a mixture of different oligonucleotide species. The mixture can include, for example, at least two, three or more different species of oligonucleotide. Each surface that is exposed to the solution therefore reacts with the solution to create a uniform density of immobilized sequences over the whole of the exposed solid support. As such, a portion of the surface having a mixture of different immobilized sequences can be surrounded by an area of the surface having a mixture of the same immobilized sequences. A suitable density of amplification oligonucleotides is at least 1 fmol/mm$^2$ ($6 \times 10^{10}$ per cm$^2$), or more optimally at least 10 fmol/mm$^2$ ($6 \times 10^{11}$ per cm$^2$). The density of the capture oligonucleotides can be controlled to give an optimum cluster density of $10^6$-$10^9$ clusters per cm$^2$ and optimum cluster brightness. The ratio of capture oligonucleotide species to the amplification oligonucleotide species can be any desired value including, but not limited to at least 1:100, 1:1000 or 1:100000 depending on the desired cluster density and brightness. Similar densities or ratios of other molecular species can be used in embodiments where molecules other than nucleic acids are attached to a surface.

In a particular embodiment, for each cluster of template molecules, a complementary copy of a single stranded polynucleotide template molecule is attached to the solid support by hybridization. Methods of hybridization for formation of stable duplexes between complementary sequences by way of Watson-Crick base-pairing are known in the art. The immobilized capture oligonucleotides can include a region of sequence that is complementary to a region or template specific portion of the single stranded template polynucleotide molecule. An extension reaction may then be carried out in which the capture sequence is extended by sequential addition of nucleotides to generate a complementary copy of the single stranded polynucleotide sequence attached to the solid support via the capture oligonucleotide. The single stranded polynucleotide sequence not immobilized to the support may be separated from the complementary sequence under denaturing conditions and removed, for example by washing.

The terms separate and separating, when used in reference to strands of a nucleic acid, refer to the physical dissociation of the DNA bases that interact within for example, a Watson-Crick DNA-duplex of the single stranded polynucleotide sequence and its complement. The terms also refer to the physical separation of these strands. Thus, the term can refer to the process of creating a situation wherein annealing of another primer oligonucleotide or polynucleotide sequence to one of the strands of a duplex becomes possible. After the first extension reaction, the duplex is immobilized through a single 5' attachment, and hence strand separation can result in loss of one of the strands from the surface. In cases where both strands of the duplex are immobilized, separation of the strands means that the duplex is converted into two immobilized single strands.

In one aspect of the invention, one or more of the amplification primers can be modified to prevent hybridization of a region or template specific portion of the single stranded polynucleotide molecule. Alternatively or additionally, one or more of the amplification primers may be modified to prevent extension of the primer during one or more extension reactions, thus preventing copying of the hybridized templates. These modifications can be temporary or permanent.

Generally, the capture sequences will include a region of the same sequence as the plurality of amplification oligonucleotides. Once the 3' end of the extended immobilized template copy has hybridized to one of the amplification primers and been extended, the resulting duplex will be immobilized at both ends and all of the bases in the capture oligonucleotide sequence will have been copied. Thus the capture oligonucleotide may include both the amplification primer sequence, plus a further sequence that is complementary to the end of the template. Typically the sequence complementary to the end of the template will not be present in any of the amplification primers. Alternatively, the amplification primers can contain the sequences complementary to the ends of the single stranded templates, but the amplification primers can be reversibly blocked to prevent hybridization and/or extension during one or more extension step, such as a first extension step in a particular amplification process.

According to one aspect of the invention, one or more of the amplification primers may include a modification that acts as a reversible block to either template hybridization or extension or both. By way of non-limiting example, such modifications can be presence of an additional sequence of nucleotides that is complementary to the amplification primer. This additional sequence can be present in a portion of the amplification primer and thus acts as an intramolecular hairpin duplex, or a 3' blocking group that prevents extension of the primer. Alternatively, the additional sequence can be found on a separate oligonucleotide that hybridizes to the amplification primer. A particular feature of such a modification is that it can be removed, altered or reversed such that the functionality of the modified primer oligonucleotide is restored and the primer is able to undergo hybridization and extension during later steps of the methods. Among other examples, the blocking group may be a small chemical species such as a 3' phosphate moiety that can be removed enzymatically, may be an a basic nucleotide such that the 3' end of the primer is not capable of hybridization (and thereby extension), or may be a sequence of nucleotides that can be selectively excised from the immobilized strands, for example, using restriction endonucleases that selectively cleave particular sequences or deglycosylases that selectively cleave oligonucleotides having exogenous bases such as uracil deoxyribonucleotides or 8-oxoguanine.

In one embodiment a plurality of three types of oligonucleotides (for example comprising capture sequences, forward and reverse primers) are immobilized to a solid support. Alternatively the three oligonucleotides may be forward amplification, blocked forward amplification and reverse amplification, where the unblocked forward primer acts as the capture sequence.

The single stranded polynucleotide molecules may have originated in single-stranded form, as DNA or RNA or may have originated in double-stranded DNA (dsDNA) form (e.g. genomic DNA fragments, PCR and amplification products and the like). Thus a single stranded polynucleotide may be the sense or antisense strand of a polynucleotide duplex. Methods of preparation of single stranded polynucleotide molecules suitable for use in the method of the invention using standard techniques are well known in the art. The precise sequence of the primary polynucleotide molecules may be known or unknown during different steps of the methods set forth herein. It will be understood that a double stranded polynucleotide molecule can be hybridized to an immobilized capture oligonucleotide as exemplified herein for single stranded polynucleotide molecules, so long as a single stranded region of the double stranded polynucleotide is available and at least partially complementary to the capture oligonucleotide sequence.

An exemplary method for the isolation of one strand of a double stranded molecular construct is described herein. A sample of unknown sequence may be fragmented and have barcode sequences attached at both ends of the fragment. Adapters are then attached to the ends of each fragment. One strand of the adapters may contain a moiety for surface immobilization, for example a biotin that can be captured onto a streptavidin surface. The adapters may be mismatch adapters, for example as described in co-pending application US 2007/0128624, the contents of which are incorporated herein by reference in their entirety. Amplification of the mismatch or forked adapters using a pair of amplification primers, one of which carries a biotin modification means that one strand of each duplex carries a biotin modification. Immobilization of the strands onto a streptavidin surface means that the non-biotinylated strand can be eluted simply by denaturation/strand separation. The eluted constructs will be in single stranded form and upon exposure to hybridization conditions can be used to hybridize against the immobilized capture sequences which can be extended.

In a particular embodiment, the single stranded polynucleotide molecules are DNA molecules. More particularly, the single stranded polynucleotide molecules represent genomic DNA molecules, or amplicons thereof, which include both intron and exon sequence (coding sequence), as well as non-coding regulatory sequences such as promoter and enhancer sequences. Still yet more particularly, the single stranded polynucleotide molecules are human genomic DNA molecules, or amplicons thereof.

In a particular embodiment, a single stranded target polynucleotide molecule has at least two regions of known sequence. Yet more particularly, the 5' and 3' termini of the single stranded polynucleotide molecule will have the regions of known sequence such that the single stranded polynucleotide molecule will be of the structure:

5'[known sequence I]-[barcode sequence]-[known sequence II]-[target polynucleotide sequence]-[known sequence III]-[barcode sequence]-[known sequence IV]-3'

Typically "known sequence I", "known sequence II", "known sequence III", and "known sequence IV" will consist of more than 20, or more than 40, or more than 50, or more than 100, or more than 300 consecutive nucleotides. The precise length of the four sequences may or may not be identical. The primer binding sequences generally will be of known sequence and will therefore particularly be complementary to a sequence within "known sequence I", "known sequence II", "known sequence III", and "known sequence IV" of the single stranded polynucleotide molecule. The length of the primer binding sequences need not be the same as those of known sequence I-IV, and may be shorter, being particularly 16-50 nucleotides, more particularly 16-40 nucleotides and yet more particularly 20-30 nucleotides in length. Known sequences I-IV can be the same or different for each other.

Methods of hybridization for formation of stable duplexes between complementary sequences by way of Watson-Crick base pairing are known in the art. A region or part of the single stranded polynucleotide template molecules can be complementary to at least a part of the immobilized capture sequence oligonucleotides. Since the amplification oligonucleotides are either modified to prevent hybridization and/or extension, or are non-complementary to the known ends of the template strands, only the capture sequences will be capable of hybridization and extension. An extension reaction may then be carried out wherein the capture sequence primer is extended by sequential addition of nucleotides to generate a complementary copy of the single stranded template polynucleotide attached to the solid support via the capture sequence oligonucleotide. The single stranded template polynucleotide sequence not immobilized to the support may be separated from the complementary sequence under denaturing conditions and removed, for example by washing. The distance between the individual capture sequence oligonucleotides on the surface therefore controls the density of the single stranded template polynucleotides and hence the density of clusters formed later on the surface is also controlled.

In certain embodiments in which the modified forward primer oligonucleotides are blocked and are unable to be extended, generally all of the amplification primer oligonucleotides will hybridize to the single stranded template polynucleotides. When the extension reaction is carried out only the unmodified forward capture primer oligonucleotides are extended by sequential addition of nucleotides to generate a complementary copy of the single stranded template polynucleotide attached to the solid support via the unmodified forward primer oligonucleotide. The single stranded template polynucleotide sequences not hybridized to the support may be separated from the un-extended blocked forward primer oligonucleotides under denaturing conditions and removed, for example by washing with a chemical denaturant such as formamide. The distance between the individual unmodified forward primer oligonucleotides on the surface therefore controls the density of the single stranded template polynucleotides and hence the density of clusters formed later on the surface is also controlled.

Following the attachment of the complementary single stranded template polynucleotides, the modified/blocked primers can be treated to reverse, remove or alter the modification such that they become functionally equivalent to the unmodified forward primer oligonucleotides. For example, the double stranded structure may be removed either by denaturation, for example by heating or treatment with an alkaline solution when it is formed by a separate hybridized polynucleotide. Alternatively, where the hybridized polynucleotide is covalently linked, enzymatic digestion could be used to sequence-selectively cleave the strand, followed by denaturation. Such methods for removing the double stranded structure are known in the art and would be apparent to the skilled person (Sambrook and Russell, Molecular Cloning, A Laboratory Manual, third edition, Cold Spring Harbor Laboratory Press (2001)).

In one embodiment of the invention, the single stranded template polynucleotide molecule can be attached to the solid support by ligation to double stranded primers immobilized to the solid support using ligation methods known in the art (Sambrook and Russell, supra). Such methods utilize ligase enzymes such as DNA ligase to effect or catalyze the joining of the ends of the two polynucleotide strands, in this case, the single stranded template polynucleotide molecule and the primer oligonucleotide ligate such that covalent linkages are formed. In this context "joining" means covalent linkage of two polynucleotide strands that were not previously covalently linked. Thus, an aim of the invention can also be achieved by modifying the 3' end of a subset of primer oligonucleotides such that they are unable to ligate to the single stranded template polynucleotides. By way of non-limiting example, the addition of 2'3'dideoxy AMP (dideoxyAMP) by the enzyme terminal deoxynucleotidyl transferase (TdT) effectively prevents T4 DNA ligase from ligating treated molecules together.

An alternative method would be to have the capture sequences as duplex strands and the amplification sequences as single strands. Upon ligation of the single strands to the capture duplexes (which would be the only immobilized species carrying a free 5' phosphate) the 3' end of the immobilized strand can be extended as described above. Upon denaturation of the hybridized template sequence, amplification of the immobilized strand can proceed as described. Other such methods for attaching single strands will be apparent to others skilled in the art.

In a next step according to particular embodiments of the present invention, suitable conditions are applied to the immobilized single stranded polynucleotide molecule and the plurality of amplification primer oligonucleotides such that the single stranded polynucleotide molecule hybridizes to an amplification primer oligonucleotide to form a complex in the form of a bridge structure. Suitable conditions such as neutralizing and/or hybridizing buffers are well known in the art (See Sambrook et al., supra; Ausubel et al., Current Protocols in Molecular Biology, John Wiley and Sons, Baltimore, Md. (1998)). The neutralising and/or hybridising buffer may then be removed.

Next by applying suitable conditions for extension an extension reaction is performed. The primer oligonucleotide of the complex is extended by sequential addition of nucleotides to generate an extension product complimentary to the single stranded polynucleotide molecule. The resulting duplex is immobilized at both 5' ends such that each strand is immobilized.

Suitable conditions such as extension buffers/solutions comprising an enzyme with polymerase activity are well known in the art (See Sambrook et al., supra; Ausubel et al. supra). In a particular embodiment dNTP's may be included in the extension buffer. In a further embodiment dNTP's could be added prior to the extension buffer. This bridge amplification technique can be carried out as described, for example, in Adessi et al. (U.S. Pat. No. 7,115,400), and Kawashima et al. (U.S. patent application number 2005/0100900), the contents of which are incorporated herein by reference.

Examples of enzymes with polymerase activity which can be used in the present invention are DNA polymerase (Klenow fragment, T4 DNA polymerase), heat-stable DNA polymerases from a variety of thermostable bacteria (such as Taq, VENT, Pfu, or Tfl DNA polymerases) as well as their genetically modified derivatives (TaqGold, VENTexo, or Pfu exo). A combination of RNA polymerase and reverse transcriptase can also be used to generate the extension products. Particularly the enzyme has strand displacement activity, more particularly the enzyme will be active at a pH of about 7 to about 9, particularly pH 7.9 to pH 8+, yet more particularly the enzymes are Est or Klenow.

The nucleoside triphosphate molecules used are typically deoxyribonucleotide triphosphates, for example dATP, dTTP, dCTP, dGTP, or are ribonucleoside triphosphates for example ATP, UTP, CTP, GTP, The nucleoside triphosphate molecules may be naturally or non-naturally occurring.

After the hybridization and extension steps, the support and attached nucleic acids can be subjected to denaturation conditions. A flow cell can be used such that, the extension buffer is generally removed by the influx of the denaturing buffer. Suitable denaturing buffers are well known in the art (See Sambrook et al.; Ausubel et al. supra). By way of example it is known that alterations in pH and low ionic strength solutions can denature nucleic acids at substantially isothermal temperatures. Formamide and urea form new hydrogen bonds with the bases of nucleic acids disrupting hydrogen bonds that lead to Watson-Crick base pairing. In a particular embodiment the concentration of formamide is 50% or more. These result in single stranded nucleic acid molecules. If desired, the strands may be separated by treatment with a solution of very low salt (for example less than 0.01 M cationic conditions) and high pH (>12) or by using a chaotropic salt (e.g. guanidinium hydrochloride). In a particular embodiment a strong base is used. A strong base is a basic chemical compound that is able to deprotonate very weak acids in an acid base reaction. The strength of a base is indicated by its pK.sub.b value, compounds with a $pK_b$ value of less than about 1 are called strong bases and are well known to one skilled in the art. In a particular embodiment the strong base is Sodium Hydroxide (NaOH) solution used at a concentration of from 0.05 M to 0.25 M, particularly 0.1 M.

Following the hybridization, extension and denaturation steps exemplified above, two immobilized nucleic acids will be present, the first being the first template single stranded polynucleotide molecule (that was initially immobilized) and the second being a nucleic acid complementary thereto, extending from one of the immobilized primer oligonucleotides. Both the original immobilized single stranded polynucleotide molecule and the immobilized extended primer oligonucleotide formed are then able to initiate further rounds of amplification by subjecting the support to further cycles of hybridization, extension and denaturation.

It may be advantageous to perform optional washing steps in between each step of the amplification method. For example an extension buffer without polymerase enzyme with or without dNTP's could be applied to the solid support before being removed and replaced with the full extension buffer.

Such further rounds of amplification can be used to produce a nucleic acid colony or cluster comprising multiple immobilized copies of the single stranded polynucleotide sequence and its complementary sequence.

The initial immobilization of the single stranded polynucleotide molecule means that the single stranded polynucleotide molecule can hybridize with primer oligonucleotides located at a distance within the total length of the single stranded polynucleotide molecule. Other surface bound primers that are out of reach will not hybridize to the polynucleotide. Thus the boundary of the nucleic acid colony or cluster formed is limited to a relatively local area surrounding the location in which the initial single stranded polynucleotide molecule was immobilized.

Once more copies of the single stranded polynucleotide molecule and its complement have been synthesized by carrying out further rounds of amplification, i.e. further rounds of hybridization, extension and denaturation, then the boundary of the nucleic acid colony or cluster being generated will be able to be extended further, although the boundary of the colony formed is still limited to a relatively local area around the location in which the initial single stranded polynucleotide molecule was immobilized. For example the size of each amplified cluster may be 0.5-5 microns.

It can thus be seen that the method of the present invention allows the generation of a plurality of nucleic acid colonies from multiple single immobilized single stranded polynucleotide molecules and that the density of these colonies can be controlled by altering the proportions of modified capture/amplification oligonucleotides used to graft the surface of the solid support.

In one embodiment, the hybridization, extension and denaturation steps are all carried out at the same, substantially isothermal temperature. For example the temperature is from 37° C. to about 75° C., particularly from 50° C. to 70° C., yet more particularly from 60° C. to 65° C. In a particular embodiment the substantially isothermal temperature may be the optimal temperature for the desired polymerase.

In a particular aspect, the method according to the first aspect of the invention is used to prepare clustered arrays of nucleic acid colonies, analogous to those described in U.S. Pat. No. 7,115,400, US 2005/0100900 A1, WO 00/18957 and WO 98/44151 (the contents of which are herein incorporated by reference), by solid-phase amplification.

In yet another aspect more than one capture sequences and more than two amplification sequences, for example, at least three or four or more, different amplification primer sequences may be grafted to the solid support. In this manner more than one library, with common sequences which differ between the libraries, could be utilized to prepare clusters, such as, for example libraries prepared from two different patients. Whilst the cluster may overlap in space, they would be able to be sequenced one after the other due to the differences between the ends of the templates. For example, two different samples can be captured using two different capture sequences. These can be amplified from the same two amplification primers. The samples can be differentiated due to the two different capture sequences, which can be used as the sites for hybridization of two different sequencing primers. The use of different capture sequences thereby gives rise to a method of sample indexing using different sequencing primers.

Clustered arrays formed by the methods of the invention are suitable for use in applications usually carried out on ordered arrays such as micro-arrays. Such applications by way of non-limiting example include hybridization analysis, gene expression analysis, protein binding analysis, sequencing, genotyping, nucleic acid methylation analysis and the like. The clustered array may be sequenced before being used for downstream applications such as, for example, hybridization with fluorescent RNA or binding studies using fluorescent labelled proteins.

Sequencing Methods

The invention also encompasses methods of sequencing amplified nucleic acids generated by solid-phase amplification. Thus, the invention provides a method of nucleic acid sequencing comprising amplifying a pool of nucleic acid templates using solid-phase amplification as described above and carrying out a nucleic acid sequencing reaction to determine the sequence of the whole or a part of at least one amplified nucleic acid strand produced in the solid-phase amplification reaction.

Sequencing can be carried out using any suitable sequencing technique. A particularly useful method is one wherein nucleotides are added successively to a free 3' hydroxyl group, resulting in synthesis of a polynucleotide chain in the 5' to 3' direction. The nature of the nucleotide added may be determined after each nucleotide addition or at the end of the sequencing process. Sequencing techniques using sequencing by ligation, wherein not every contiguous base is sequenced, and techniques such as massively parallel signature sequencing (MPSS) where bases are removed from, rather than added to the strands on the surface are also within the scope of the invention.

The initiation point for the sequencing reaction may be provided by annealing of a sequencing primer to a product of the solid-phase amplification reaction. In this connection, one or both of the adaptors added during formation of the template library may include a nucleotide sequence which permits annealing of a sequencing primer to amplified products derived by whole genome or solid-phase amplification of the template library.

The products of solid-phase amplification reactions wherein both forward and reverse amplification primers are covalently immobilized on the solid surface are so-called bridged structures formed by annealing of pairs of immobilized polynucleotide strands and immobilized complementary strands, both strands being attached to the solid support at the 5' end. Arrays comprised of such bridged structures provide inefficient templates for typical nucleic acid sequencing techniques, since hybridization of a conventional sequencing primer to one of the immobilized strands is not favored compared to annealing of this strand to its immobilized complementary strand under standard conditions for hybridization.

In order to provide more suitable templates for nucleic acid sequencing, it may be advantageous to remove or displace substantially all or at least a portion of one of the immobilized strands in the bridged structure in order to generate a template which is at least partially single-stranded. The portion of the template which is single-stranded will thus be available for hybridization to a sequencing primer. The process of removing all or a portion of one immobilized strand in a 'bridged' double-stranded nucleic acid structure may be referred to herein as linearization, and is described in further detail in WO07010251, the contents of which are incorporated herein by reference in their entirety.

Bridged template structures may be linearized by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease (for example 'USER', as supplied by NEB, part number M5505S), or by exposure to heat or alkali, cleavage of ribonucleotides incorporated into amplification products otherwise comprised of deoxyribonucleotides, photochemical cleavage or cleavage of a peptide linker.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution or heat, will be apparent to the skilled reader with reference to standard molecular biology protocols (Sambrook et al., supra; Ausubel et al. supra). Denaturation results in the production of a sequencing template which is partially or substantially single-stranded. A sequencing reaction may then be initiated by hybridization of a sequencing primer to the single-stranded portion of the template.

Thus, the invention encompasses methods wherein the nucleic acid sequencing reaction comprises hybridizing a sequencing primer to a single-stranded region of a linearized amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One sequencing method which can be used in accordance with the invention relies on the use of modified nucleotides having removable 3' blocks, for example as described in WO04018497, US 2007/0166705A1 and U.S. Pat. No. 7,057,026, the contents of which are incorporated herein by reference in their entirety. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides, it is possible to deduce the DNA sequence of the DNA template. Such reactions can be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may carry a label to facilitate their detection. A fluorescent label, for example, may be used for detection of modified nucleotides. Each nucleotide type may thus carry a different fluorescent label, for example, as described in WO07/35368, the contents of which are incorporated herein by reference in their entirety. The detectable label need not, however, be a fluorescent label. Any label can be used which allows the detection of an incorporated nucleotide.

One method for detecting fluorescently labeled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in WO07/23744, the contents of which are incorporated herein by reference in their entirety.

The invention is not intended to be limited to use of the sequencing method outlined above, as essentially any sequencing methodology which relies on successive incorporation of nucleotides into a polynucleotide chain can be used. Suitable alternative techniques include, for example, the Genome Sequencers from Roche/454 Life Sciences (Margulies et al. (2005) Nature, 437:376-380; U.S. Pat. Nos. 6,274,320; 6,258,568; 6,210,891), and the SOLiD system from Applied Biosystems (solid.appliedbiosystems.com), and the sequencer from Ion Torrent (www.iontorrent.com).

Incorporation by Reference

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method for validating the sequence of a nucleic acid analyte of interest in a multiplex sequencing reaction, the method comprising:
   i) detecting the presence of two or more identifier sequences that are uniquely associated with the nucleic acid analyte of interest,
      wherein at least a first identifier sequence is incorporated into a 5' portion of the nucleic acid analyte of interest and wherein at least a second identifier sequence is incorporated into a 3' portion of the nucleic acid analyte of interest, and
      wherein the first and second identifier sequences have four or more nucleotides and are different;
   ii) sequencing the first identifier sequence, the nucleic acid analyte of interest and the second identifier sequence; and
   iii) validating the sequence of the nucleic acid analyte of interest by analyzing both identifiers and excluding the sequences of those nucleic acid analytes of interest containing only one identifier or an incorrect pair of identifiers from sequence analysis of the multiplex sequencing reaction.

2. The method of claim 1, wherein the identifier sequences are nucleic acid sequence tags.

3. The method of claim 2, wherein the identifier sequences are barcode sequences.

4. The method of claim 3, wherein the barcode sequences are from 4 to 20 nucleotides.

5. The method of claim 4, wherein t barcode sequences are designed to have no homopolymer regions.

6. The method of claim 1, wherein the nucleic acid analyte of interest is on the surface of a flow cell.

* * * * *